US012748111B2

(12) United States Patent
Ruf et al.

(10) Patent No.: US 12,748,111 B2
(45) Date of Patent: Sep. 29, 2026

(54) METHODS FOR DETECTION OF PATHOGENIC ANTIPHOSPHOLIPID ANTIBODIES AND FOR IDENTIFICATION OF INHIBITORS

(71) Applicants: UNIVERSITÄTSMEDIZIN DER JOHANNES GUTENBERG-UNIVERSITÄT MAINZ, Mainz (DE); THE SCRIPPS RESEARCH INSTITUTE, La Jolla, CA (US)

(72) Inventors: Wolfram Ruf, San Diego, CA (US); Nadine Müller-Calleja, Mainz (DE); Karl Lackner, Mainz (DE); Luc Teyton, La Jolla, CA (US)

(73) Assignees: UNIVERSITÄTSMEDIZIN DER JOHANNES GUTENBERG-UNIVERSITÄT MAINZ, Mainz (DE); THE SCRIPPS RESEARCH INSTITUTE, La Jolla, CA (US)

( * ) Notice: Subject to any disclaimer, the term of this patent is extended or adjusted under 35 U.S.C. 154(b) by 1072 days.

(21) Appl. No.: 17/789,823

(22) PCT Filed: Dec. 9, 2020

(86) PCT No.: PCT/EP2020/085278
§ 371 (c)(1),
(2) Date: Jun. 29, 2022

(87) PCT Pub. No.: WO2021/136639
PCT Pub. Date: Jul. 8, 2021

(65) Prior Publication Data

US 2023/0043394 A1 Feb. 9, 2023

Related U.S. Application Data

(60) Provisional application No. 62/955,060, filed on Dec. 30, 2019.

(51) Int. Cl.
*G01N 33/53* (2006.01)
*G01N 33/564* (2006.01)
*G01N 33/92* (2006.01)

(52) U.S. Cl.
CPC ........... *G01N 33/564* (2013.01); *G01N 33/92* (2013.01); *G01N 2333/96461* (2013.01); *G01N 2405/04* (2013.01); *G01N 2800/101* (2013.01)

(58) Field of Classification Search
None
See application file for complete search history.

(56) References Cited

U.S. PATENT DOCUMENTS

2007/0141625 A1* 6/2007 Santos ................ G01N 33/564 435/7.1

FOREIGN PATENT DOCUMENTS

EP 1722229 A1 11/2006
WO 2010121714 A1 10/2010

OTHER PUBLICATIONS

Lederman et al. "A single amino acid substitution in a common African allele of the CD4 molecule ablates binding of the monoclonal antibody, OKT4" Mol Immunol. Nov. 1991;28(11): pp. 1171-1181 (Year: 1991).*
Colman et al. Research im Immunology, 1994; 145(1):pp. 33-36 (Year: 1994).*
Harlow, E. and Lan D., Antibodies: A Laboratory Manual (1988) Cold Spring Harbor Laboratory Press, Cold Spring Harbor, NY, pp. 23-26. (Year: 1988).*
Alessandri, C., et al. "New autoantigens in the antiphospholipid syndrome." Autoimmunity reviews 10.10 (2011): pp. 609-616.
Shoenfeld, Y., et al. "Autoantibody explosion in antiphospholipid syndrome." Journal of autoimmunity 30.1-2 (2008): pp. 74-83.

* cited by examiner

*Primary Examiner* — Gary Counts
(74) *Attorney, Agent, or Firm* — SALIWANCHIK, LLOYD & EISENSCHENK

(57) ABSTRACT

The present invention provides methods for detecting whether a subject suffers from an autoimmune disease, such as, for example, antiphospholipid syndrome (APS), by detecting antiphospholipid antibodies (aPL) in a sample using a novel target, the lysobisphosphatidic acid (LBPA) bound to the endothelial protein C receptor (EPCR) or an LBPA-binding fragment thereof. Furthermore, methods for identifying an inhibitor of endothelial protein C receptor (EPCR) function in autoimmune disease, preferably without a side effect on EPCR regulatory function in coagulation, and a method for producing a pharmaceutical composition comprising the steps of identifying a potential inhibitor, and suitably formulating said potential inhibitor into a pharmaceutical composition are provided. Methods for treating and/or preventing an autoimmune disease, such as, for example, antiphospholipid syndrome, in a subject are also provided.

9 Claims, 24 Drawing Sheets

E

F

D

E

F

G

F (cont.)

G

H

A

B

C

D

E

F

G

H

I

J

METHODS FOR DETECTION OF PATHOGENIC ANTIPHOSPHOLIPID ANTIBODIES AND FOR IDENTIFICATION OF INHIBITORS

CROSS REFERENCE TO RELATED APPLICATIONS

This application is a National Stage Application of International Application Number PCT/EP2020/085278, filed Dec. 9, 2020; which claims priority to U.S. Provisional Patent Application No. 62/955,060, filed Dec. 30, 2019.

FIELD OF THE INVENTION

The present invention relates to methods for detecting whether a subject suffers from an autoimmune disease, such as, for example, antiphospholipid syndrome (APS), by detecting antiphospholipid antibodies (aPL) in a sample using a novel target, the lysobisphosphatidic acid (LBPA) bound to the endothelial protein C receptor (EPCR) or an LBPA-binding fragment thereof. Furthermore, the present invention relates to methods for identifying an inhibitor of endothelial protein C receptor (EPCR) function in autoimmune disease, preferably without a side effect on EPCR regulatory function in coagulation, and a method for producing a pharmaceutical composition comprising the steps of identifying a potential inhibitor, and suitably formulating said potential inhibitor into a pharmaceutical composition. Moreover, the present invention relates to said inhibitor as identified or said pharmaceutical composition for use in the prevention and/or treatment of an autoimmune disease, such as, for example, an antiphospholipid syndrome, in a subject. Furthermore, the present invention relates to a method for treating and/or preventing an autoimmune disease, such as, for example, antiphospholipid syndrome, in a subject.

BACKGROUND

Antiphospholipid syndrome (APS) is an acquired autoimmune disease in which a deficient control of the immune system leads to an increased tendency of the blood to coagulate. The resulting blood coagulation (thromboses) can subsequently lead to reduced blood flow (ischemia) to the affected tissue and trigger complications such as strokes, heart attacks or abortions. Although lipid-reactive antibodies also transiently appear in infectious diseases, clonal evolution of persistent antiphospholipid antibodies (aPL) in autoimmune diseases causes severe thrombo-embolic events, pregnancy morbidity, and fetal loss in the antiphospholipid syndrome (APS) (1).

Reactivity with cardiolipin is used to identify aPL, but aPL recognize a variety of anionic phospholipids and blood proteins, including β2-glycoprotein I (β2GPI). These complex reactivities have hampered the definition of a precise mechanism that causes the spectrum of APS-related pathologies (1, 2) and the development of autoimmune disease (3, 4). Clonal expansion of monoclonal aPL leads to protein cross-reactivity (5), but lipid recognition is sufficient to cause pregnancy complications (6) and thrombosis in mice (7), both of which involve a crosstalk of the innate immune defense complement and coagulation pathways (6, 8).

By binding to EPCR expressed by myeloid cells, aPL target a crucial toggle switch that controls coagulation and innate immune signalling. PAR2 activation by the TF-FVIIa-FXa-EPCR complex supports TLR4-mediated induction of interferon-regulated genes (16), but competition for EPCR ligand occupancy by the anticoagulant activated Protein C-FV-Protein S complex attenuates TF-dependent PAR2 signalling (37). Deregulated interferon signalling drives autoimmunity and by targeting EPCR aPL directly induce interferon signaling responses in myeloid cells, while mice with a disabled EPCR signalling pathway are protected from autoimmune aPL development.

Genetic or pharmacological inhibition of the antigenic target EPCR-LBPA attenuates aPL-induced pathologies in mice. Innate immune cell-expressed EPCR engagement by aPL induces interferon-regulated anti-microbial responses and drives interferon-dependent B cell expansion and the development of autoimmunity. Thus, aPL recognize a single lipid-protein receptor complex required for the pathogenesis and complications of this autoimmune disease.

US 2007-0141625A1 relates to a method for detecting autoantibodies against endothelial protein C/activated protein C receptor (EPCR) in a sample by its detection and in vitro quantification.

Sorice et al. (in: Evidence for anticoagulant activity and beta2-GPI accumulation in late endosomes of endothelial cells induced by anti-LBPA antibodies. Thromb Haemost. 2002 April; 87(4):735-41. PMID: 12008959) disclose that anti-LBPA antibodies and IgG from APS patients affect the distribution of intracellular β2GPI in endothelial cell culture as well as the coagulation system. Further, they suggest that LBPA is a target for aPl and is involved in the immunopathogenesis of APS.

Alessandri et al. (in: Anti-lysobisphosphatidic acid antibodies in patients with antiphospholipid syndrome and systemic lupus erythematosus. Clin Exp Immunol. 2005 April; 140(1):173-80. doi: 10.1111/j.1365-2249.2005.02727.x. PMID: 15762889) describe LBPA antibodies as biomarkers in antiphospholipid syndrome patients.

Olivieri et al. (in: Clinical value of antibodies to lysobisphosphatidic acid in patients with primary antiphospholipid syndrome. Reumatismo. 2010 April-June; 62(2):107-12. Italian. doi: 10.4081/reumatismo.2010.107. PMID: 20657887) investigate anti-LBPA for its clinical value and reveals that anti-LBPA antibodies cannot be used to diagnose APS.

The prior art discloses that endothelial protein C receptor (EPCR) and lysobisphosphatidic acid (LBPA) or antibodies directed against endothelial protein C receptor (EPCR) or lysobisphosphatidic acid (LBPA) can be used as biomarkers to diagnose APS in patients. However, it is disclosed that antibodies against lysobisphosphatidic acid (LBPA) have no advantage as biomarkers compared to the analysis of other antibodies, e.g. against cardiolipin.

Thus, it is therefore an object of the present invention to provide a reliable and robust method for the detection of autoimmune disease, such as, for example, antiphospholipid syndrome (APS), in particular primary or secondary APS, based on binding of antiphospholipid antibodies (aPL).

A further object of the present invention is to provide a method for identification of potential inhibitors that prevent the aPL-pathogenic signalling.

Another object is the provision of a method for producing a pharmaceutical composition, wherein inter alia such an inhibitor is comprised.

Yet another object of the present invention is then to provide a method for treatment and/or prevention of an autoimmune disease, for example antiphospholipid syndrome (APS), in particular primary or secondary APS, in a subject by administering the pharmaceutical composition containing said inhibitor to said subject.

Other aspects and objects will become apparent to the person of skill upon studying the following description of the invention.

BRIEF DESCRIPTION OF THE INVENTION

Surprisingly, the inventors in the context of the present invention identified endosomal lysobisphosphatidic acid (LBPA) and the presentation thereof by the CD1d-like endothelial protein C receptor (EPCR) as a so far unknown disease-causing cell surface antigen recognized by aPL. By intersecting with the innate immune and coagulation signalling function of EPCR, aPL engage with EPCR for endosomal trafficking and the initiation of prothrombotic and proinflammatory signalling.

The inventors were further able to show that the interaction of endothelial protein C receptor (EPCR) and LPBA is critical for the course of the antiphospholipid syndrome. This surprising discovery enables the use of the EPCR-LBPA complex as a novel target for diagnostic screening procedures and in screening procedures for the production of drugs that can be used to treat and prevent the antiphospholipid syndrome.

In a first aspect, the invention solves the above object by providing a method for detecting whether a subject suffers from an autoimmune disease, comprising detecting binding of antiphospholipid antibodies (aPL) in a biological sample obtained from said subject to lysobisphosphatidic acid (LBPA) bound to endothelial protein C receptor (EPCR) or said LBPA-binding fragment thereof, wherein said binding of aPL to said lysobisphosphatidic acid (LBPA) bound to endothelial protein C receptor (EPCR) or an LBPA-binding fragment thereof detects an autoimmune disease in said subject.

In a second aspect, the invention relates to a method for identifying an inhibitor of endothelial protein C receptor (EPCR) function/activity in an autoimmune disease, preferably without interfering with its function in coagulation, comprising providing a biological sample comprising an EPCR protein or an lysobisphosphatidic acid (LBPA)-binding fragment thereof, contacting a potential inhibitor with said sample, and testing binding of LBPA to said EPCR protein or said LBPA-binding fragment thereof in the presence or absence of said potential inhibitor, and identifying said potential inhibitor based on said LBPA-binding as tested.

In a third aspect, the invention relates to a method for identifying an inhibitor of endothelial protein C receptor (EPCR) function in autoimmune disease which preferably does not interfere with EPCR regulatory function in coagulation, comprising providing a biological sample comprising an EPCR protein or an lysobisphosphatidic acid (LBPA)-binding part thereof, binding of LBPA to said EPCR protein or said LBPA-binding fragment thereof to form an EPCR-LBPA-complex, contacting a potential inhibitor with said sample, and testing binding of an antiphospholipid antibody (aPL) or cellular effects/functions in the presence or absence of said potential inhibitor, and identifying said potential inhibitor based on interference with said aPL-binding or cellular functions as tested.

In a fourth aspect, the invention relates to a method for producing a pharmaceutical composition, comprising the steps of identifying a potential inhibitor or inhibitor as described herein, and suitably formulating said potential inhibitor or inhibitor into a pharmaceutical composition.

In a fifth aspect, the invention relates to an inhibitor as identified or a pharmaceutical composition as described herein for use in the prevention and/or treatment of an autoimmune disease in a subject.

In a sixth aspect, the invention relates to a method of treating and/or preventing an autoimmune disease, such as, for example, antiphospholipid syndrome, in particular primary or secondary APS, in a subject, said method comprising administering to said subject in need of such treatment and/or prevention an effective amount of an inhibitor as identified and described herein or a pharmaceutical composition as described herein.

DETAILED DESCRIPTION OF THE INVENTION

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

As mentioned above, in the first aspect thereof, the present invention relates to a method for detecting whether a subject suffers from an autoimmune disease, comprising detecting binding of antiphospholipid antibodies (aPL) in a biological sample obtained from said subject to lysobisphosphatidic acid (LBPA) bound to endothelial protein C receptor (EPCR) or an LBPA-binding fragment thereof, wherein said binding of aPL to said lysobisphosphatidic acid (LBPA) bound to endothelial protein C receptor (EPCR) or an LBPA-binding fragment thereof detects the presence of an autoimmune disease in said subject.

An "LBPA-binding fragment" as used herein shall mean a part or fragment of the endothelial protein C receptor (EPCR) that is sufficient so that said LBPA-binding fragment is still capable of, preferably, binding lysobisphosphatidic acid (LBPA), i.e. the receptor affinity of the endothelial protein C receptor (EPCR) is retained by said LBPA-binding fragment. Included are also structural mimetics of such a binding domain. Preferably, all or part of the LBPA-binding fragment is produced recombinantly in expression suitable systems or by chemical synthesis.

While APS is the only manifestation of autoimmunity in many patients (primary APS), it also develops in in the context of other autoimmune diseases, in particular systemic lupus erythematosus (SLE) (secondary APS). Thus, preferred is an embodiment of the present invention, wherein the autoimmune disease is antiphospholipid syndrome, in particular primary or secondary APS. Further autoimmune diseases are selected from primary Sjögren syndrome, rheumatoid arthritis, systemic lupus erythematosus, and lupus nephritis, without being limited to these.

As used herein, the term "antiphospholipid antibodies (aPL)" are autoantibodies which generally bind to negatively charged phospholipids, including cardiolipin (CL) as the antigen. Included are also antigen-binding fragments of these antibodies (see also below for further description).

As used herein, the term "binding" of aPL to said LBPA bound to EPCR or an LBPA-binding fragment thereof, or binding of LBPA to EPCR or an LBPA-binding fragment thereof, or further intermolecular bonds between molecules in the context of the present invention are based on non-covalent interactions. These "non-covalent" interactions refer to chemical interactions between atoms in which they do not share electron pairs. Non-covalent interactions are classified in hydrogen bonds, Van-der-Waals interactions, hydrophobic interactions and electrostatic interactions. The presence of binding between the respective above-mentioned binding partners shall be investigated using "binding assays", based on the specific binding respectively interactions between said binding partners. There are a number of suitable binding assays, such as an enzyme-linked immunosorbent assay (ELISA), that are known to the skilled person.

Further preferred is an embodiment of the present invention, wherein said lysobisphosphatidic acid (LBPA) bound to endothelial protein C receptor (EPCR) or an LBPA-binding fragment thereof is immobilized, preferably directly or indirectly to a solid carrier material.

As used herein the term "directly" immobilized means the immobilization of an isolated and soluble endothelial protein C receptor (EPCR) or an isolated and soluble LBPA-binding fragment, wherein lysobisphosphatidic acid (LBPA) is bound thereto, and wherein said endothelial protein C receptor (EPCR) or said LBPA-binding fragment directly are immobilized covalent on the solid carrier material for example via photochemical methods. So-called photolinkers can be used, which are bound to the endothelial protein C receptor (EPCR) or said LBPA-binding fragment in order to fix the biomolecules covalently, parallel and directed on the solid carrier material. The photoreaction is triggered by UV irradiation, whereby the wavelength range above 300 nm must be used in order to avoid photolytic decomposition of the biomolecules. The photolinkers react with the substrate in a photoinduced radical reaction and the endothelial protein C receptor (EPCR) or said LBPA-binding fragment is directly immobilized on said solid carrier material.

The term "indirectly" immobilized means the fixation of cells expressing the endothelial protein C receptor (EPCR) or the LBPA-binding fragment, or part of cells presenting the endothelial protein C receptor (EPCR) or the LBPA-binding fragment on their surface on the solid carrier material, wherein lysobisphosphatidic acid (LBPA) is either already bound to the endothelial protein C receptor (EPCR) or the LBPA-binding fragment, or is added to the cell culture supernatant, so that the lysobisphosphatidic acid (LBPA) bound to endothelial protein C receptor (EPCR) or the LBPA-binding fragment is provided via fixed cells or parts thereof on their surface, wherein the cells or parts thereof are fixed on the solid carrier material. The term "cells" used in the context of the present invention means eukaryotic cells capable of expressing the endothelial protein C receptor (EPCR) or the LBPA-binding fragment. Therefore, the PROCR-Gene encoding the endothelial protein C receptor (EPCR) or a nucleic acid encoding the LBPA-binding fragment can either already be present in the cells or the cell can be transfected with the nucleic acids or a vector comprising the nucleic acids. The term "eukaryotic" includes yeast, higher plant, insect and mammalian cells. Once the nucleic acid or vector has been transfected into the corresponding cell, the cell is kept under conditions suitable for high-grade expression of the nucleic acids or the vector.

The term "solid carrier material" shall refer to any solid support material which is chemically inert and allows the direct or indirect immobilization of the endothelial protein C receptor (EPCR) or the LBPA-binding fragment to the solid support material. A large immobilization area can be achieved by using very porous materials. Furthermore, the carrier must allow substances used in the context of the present invention to flow in and out. A number of suitable carriers are known. The solid carrier material can be, for example, selected from glass, agarose, polymers, or metals, but without being limited to it.

In the second aspect, the invention relates to a method for identifying an inhibitor of endothelial protein C receptor (EPCR) function in an autoimmune disease while preferably not interfering with EPCR regulatory function in coagulation, comprising providing a biological sample comprising an EPCR protein or an lysobisphosphatidic acid (LBPA)-binding fragment thereof, contacting a potential inhibitor with said sample, and testing binding of LBPA to said EPCR protein or said LBPA-binding fragment thereof in the presence or absence of said potential inhibitor, and identifying said potential inhibitor based on said LBPA-binding as tested. This assay therefore seeks to identify inhibitors of the binding between LBPA to the EPCR protein.

In the third aspect, the invention relates to a method for identifying an inhibitor of endothelial protein C receptor (EPCR) function in autoimmune disease without interfering with EPCR regulatory function in coagulation, comprising providing a biological sample comprising an EPCR protein or an lysobisphosphatidic acid (LBPA)-binding fragment thereof, binding of LBPA to said EPCR protein or said LBPA-binding fragment thereof to form an EPCR-LBPA-complex, contacting a potential inhibitor with said sample, and testing binding of an antiphospholipid antibody (aPL) or cellular functions in the presence or absence of said potential inhibitor, and identifying said potential inhibitor based on interfering with said aPL-binding or cellular effects/functions as tested. This assay therefore seeks to identify inhibitors of the binding between the LBPA/EPCR protein complex, and the aPL, and "general" inhibitors interfering with the signalling pathway involving said complex and aPL In addition to "binding" as described above, potential inhibitors can also be identified via "cellular functions" within intact cells present in the biological sample. "Cellular functions", as used in the context of the present invention, are based on alterations in protein expression of interferon induced genes in said cells present in the biological sample in the presence or absence of the potential inhibitor. For example, both inhibitory and non-inhibitory binding partners are able to bind to the LBPA-EPCR complex, EPCR or aPL. While binding of an inhibitory binding partner, i.e. a potential inhibitor, prevents the aPL-induced interferon response, the binding of non-inhibitory binding partners does not alter the aPL-induced interferon response. The interferon response then leads to expansion of aPL producing B-cells and expression of interferon-induced genes. Interferon-induced genes comprise, but are not limited to, IRF8, GBP2, GBP6.

Preferred is an embodiment of the method according to the present invention, wherein at least one of EPCR, fragment, LBPA, said potential inhibitor and/or aPL is suitably labelled and/or immobilized.

The term "suitably labelled" as used herein means that at least one of EPCR, fragment, LBPA, said potential inhibitor and/or aPL may contain additional markers, such as non-protein molecules such as nucleic acids, sugars, or markers for radioactive or fluorescent labelling. The label is either directly or indirectly involved in generating a detectable signal.

In another preferred embodiment of the present invention, the method further comprises the step of testing said potential inhibitor as identified for being an inhibitor of endothelial protein C receptor (EPCR) function in an autoimmune disease without interference of EPCR function as a regulator of coagulation. The inventors showed that binding of aPL to the EPCR-LBPA complex leads to the internalization of the complex and pathogenic aPL signalling. The important function of EPCR as a regulator of coagulation is maintained, as EPCR binds to its agonist protein C in the absence of LBPA, wherein binding of protein C to EPCR is not prevented by the inhibitors as identified. This testing can also involve the other components of the system, LBPA, and/or aPL.

Using the term "suitably testing" in the context of the present invention, a distinction is made between suitable testing of the binding or of suitable testing of the cellular functions. A suitable testing of the binding means the detection of a generated detectable signal depending on the used label with a suitable detection system to determine whether a potential inhibitor could prevent the binding of LBPA to EPCR or the LBPA-binding fragment, or whether a potential inhibitor could prevent the binding of aPL to the LBPA-EPCR complex. For example, FRET probes can be used for suitable testing, where one binding partner is labelled with a donor fluorochrome and another binding partner is labelled with an acceptor fluorochrome. The fluorescence signal emitted can be used for very specific detection of whether the potential inhibitor to be identified prevented binding of the binding partners involved. Many other detection systems are known in the prior art. Suitable testing of the cellular functions means the detection of aPL induced interferon response or the detection of expressed aPL due to expanded B cells. The detection can be performed at the posttranscriptional or posttranslational level either by quantification of mRNA or proteins. The skilled person is aware of methods for mRNA and protein analysis.

Further preferred is an embodiment of the method according to the present invention, wherein said potential inhibitor is selected from a small molecule, a protein, a peptide, an antibody or antigen-binding fragment thereof, an enzyme, and an aptamer.

The term "small molecule" as used herein describes a class of substances with a low molecular mass, that does not exceed about 900 Dalton. Due to their small size, small molecules are partly able to penetrate into cells. Small molecules can be chemically synthesized. The term covers an extremely heterogeneous group of substances. Small molecules have a multitude of biological functions, such as signal molecules. They can be of natural (e.g. secondary metabolites) or artificial (e.g. antivirals) origin. Some small molecules are able to cross the blood-brain barrier.

The term "protein" is used to denote a polymer composed of amino acid monomers joined by peptide bonds. It refers to a molecular chain of amino acids, and does not refer to a specific length of the product and if required can be modified in vivo or in vitro, for example by glycosylation, amidation, carboxylation or phosphorylation. Amino acid chains with a length of less than approx. 100 amino acids are called "peptides". The terms "peptides", and "proteins" as used herein are included within the definition of "polypeptides". A "peptide bond" is a covalent bond between two amino acids in which the α-amino group of one amino acid is bonded to the α-carboxyl group of the other amino acid. All amino acid or polypeptide sequences, unless otherwise designated, are written from the amino terminus (N-terminus) to the carboxy terminus (C-terminus).

"Antibody" and "antibodies" refer to antigen-binding proteins that arise in the context of the immune system. The term "antibody" as referred to herein includes whole, full length antibodies and any fragment or derivative thereof in which the "antigen-binding portion" or "antigen-binding region" or single chains thereof are retained, such as a binding domain of an antibody specific for lysobisphosphatidic acid (LBPA), endothelial protein C receptor (EPCR), LBPA-binding fragment, LBPA-EPCR-complex, or antiphospholipid antibodies (aPL). A naturally occurring "antibody" (immunoglobulin) is a glycoprotein comprising at least two heavy (H) chains and two light (L) chains inter-connected by disulfide bonds. Each heavy chain is comprised of a heavy chain variable region (abbreviated herein as VH) and a heavy chain constant region. Heavy chains are classified as mu, delta, gamma, alpha, or epsilon, and define the antibody's isotype as IgM, IgD, IgG, IgA, and IgE, respectively. The heavy chain constant region is comprised of three domains, CHI, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The heavy and light chains form two regions: the Fab (fragment, antigen binding) region, also referred to as the variable (Fv) region, and the Fc (fragment, crystallizable) region. The variable regions (Fv) of the heavy and light chains contain a binding domain that interacts with an antigen. The constant (Fc) regions of the antibodies may mediate the binding to host tissues or factors, including various cells of the immune system (e.g., effector cells) and the first component (C1q) of the classical complement system. The term "Fc" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns. One suitable Fc polypeptide is derived from the human IgG1 antibody.

Fragments, derivatives, or analogs of antigen-binding proteins such as antibodies can be readily prepared using techniques well-known in the art. The term "antigen binding fragment" as used herein refers to a polypeptide that has an amino-terminal and/or carboxy-terminal deletion as compared to a corresponding full-length antigen-binding protein. Examples of fragments of antigen-binding proteins encompassed within the term "antigen-binding fragments" include a Fab fragment; a monovalent fragment consisting of the VL, VH, CL and CHI domains; a F(ab')2 fragment; a bivalent fragment comprising two Fab fragments linked by a disulfide bridge at the hinge region; a Fd fragment consisting of the VH and CHI domains; a Fv fragment consisting of the VL and VH domains of a single arm of an antibody; a dAb fragment which consists of a VH domain; an isolated complementarity determining region (CDR); and a single chain variable fragment (scFv). An antigen-binding protein or fragment or derivative thereof or fusion protein thereof may have one or more binding sites. If there is more than one binding site, the binding sites may be identical to one another or may be different. For example, a naturally occurring human immunoglobulin typically has two identical binding sites, while a “bispecific antibody” or “bifunctional antibody” has two different binding sites. Bispecific antibodies are preferred molecules of the invention and may be selected from any bispecific format known to the skilled artisan such as bites or diabodies. A “derivative” of an antigen-binding protein is a polypeptide (e.g., an antibody) that has been chemically modified, e.g., via conjugation to another chemical moiety (such as, for example polyethylene glycol or albumin, e.g., human serum albumin), phosphorylation, and/or glycosylation.

An “scFv” is a monovalent molecule that can be engineered by joining, using recombinant methods, the two domains of the Fv fragment, VL and VH, by a synthetic linker that enables them to be made as a single protein chain. Such single chain antigen-binding peptides are also intended to be encompassed within the term “antigen-binding portion.” These antibody fragments are obtained using conventional techniques known to those of skill in the art, and the fragments are screened for utility in the same manner as are intact antibodies.

The term “antigen-binding fragment” or “antigen-binding region” of an antigen-binding protein such as an antibody, or grammatically similar expressions, as used herein, refers to that region or portion that confers antigen specificity; fragments of antigen-binding proteins, therefore, include one or more fragments of an antigen-binding protein that retain the ability to specifically bind to an antigen (e.g., an HLA-peptide complex). It has been shown that the antigen-binding function of an antibody can be performed by fragments of a full-length antibody.

The term “enzyme” as used herein refers to a protein with catalytic activity.

As used herein the term “aptamer” means short single-stranded DNA or RNA oligonucleotides (25-70 bases) that can bind to a specific molecule. Aptamers commonly comprise RNA, single stranded DNA, modified RNA or modified DNA molecules. The preparation of aptamers is well known in the art and may involve, inter alia, the use of combinatorial RNA libraries to identify binding sides.

Preferred is an embodiment of the method according to the present invention, wherein said subject is a mammal, preferably a human.

Further preferred is an embodiment of the method according to the present invention, wherein said biological sample is selected from a body fluid, including blood, serum, and saliva, and a tissue, organ or cell type blood sample, a sample of blood lymphocytes and a fraction thereof.

In the fourth aspect, the invention relates to a method for producing a pharmaceutical composition, comprising the steps of identifying a potential inhibitor or inhibitor as described herein, and suitably formulating said potential inhibitor or inhibitor into a pharmaceutical composition.

As used herein the term “pharmaceutical composition” refers to a “suitable formulation” which is in such form as to permit the biological activity of an active ingredient contained therein to be effective, and which contains no additional components which are unacceptably toxic to a subject to which the composition would be administered. A pharmaceutical composition of the present invention can be administered by a variety of methods known in the art. As will be appreciated by the skilled person, the route and/or mode of administration will vary depending upon the desired results. To administer a binding compound according to the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions.

An “appropriate carrier” refers to an ingredient in a pharmaceutical formulation, other than an active ingredient, which is nontoxic to a subject. Appropriate carriers include any and all solvents, dispersion media, coatings, antibacterial and antifungal agents, isotonic and absorption delaying agents, and the like that are physiologically compatible. Administration may be, for example, intravenous, intramuscular, subcutaneous, parenteral, spinal or epidermal administration (e.g. by injection or infusion). The prevention of the presence of microorganisms can be ensured both by sterilization procedures, Supra, and by the use of various antibacterial and antifungal agents, such as parabens, chlorobutanol, phenol, sorbic acid and the like. It may also be desirable to include isotonic agents such as sugar, sodium chloride and the like in the compositions. In addition, prolonged absorption of the injectable dosage form can be achieved by using absorption retardants such as aluminium monostearate and gelatin.

Regardless of the route of administration selected, the compound(s) of the present invention, which may be used in a suitable hydrated form, and/or the pharmaceutical compositions of the present invention, are formulated into pharmaceutically acceptable dosage forms by conventional methods known to those of skilled in the art. Actual dosage levels of the active ingredients in the pharmaceutical compositions of the present invention may be varied. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In many cases, isotonic agents, for example, sugars, polyalcohols such as mannitol or sorbitol, and sodium chloride are included in the composition.

The compositions of the invention may be administered locally or systemically. Administration will generally be parenterally, e.g., intravenously; Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer’s dextrose, dextrose and sodium chloride, lactated Ringer’s, or fixed oils. Intravenous vehicles include fluid and nutrient replenishers, electrolyte replenishers (such as those based on Ringer’s dextrose), and the like. Preservatives and other additives may also be present such as, for example, antimicrobials, antioxidants, chelating agents, and inert gases and the like.

In the fifth aspect, the invention relates to an inhibitor as identified or a pharmaceutical composition as described herein for use in the prevention and/or treatment of an autoimmune disease in a subject while preferably avoiding interference with vascular protective functions of EPCR.

As used herein, the terms "preventing" or "prevention" comprise the administration of said compound(s) to said subject, preferably in a preventively effective amount to refer to reduce, no matter how slight, of a subject's predisposition or risk for developing an autoimmune disease, such as an antiphospholipid syndrome, in particular primary or secondary APS, primary Sjögren syndrome, rheumatoid arthritis, systemic lupus erythematosus, and lupus nephritis. For prevention, the subject is preferably a subject who is at risk or susceptible to the development of an autoimmune disease, such as an antiphospholipid syndrome, in particular primary or secondary APS, primary Sjögren syndrome, rheumatoid arthritis, systemic lupus erythematosus, and lupus nephritis.

The terms "treating" or "treatment", as used herein, comprise the administration of said compound(s) to said subject, preferably in a therapeutically effective amount to alleviate the disease or progression of an autoimmune disease, such as an antiphospholipid syndrome in particular primary or secondary APS, primary Sjögren syndrome, rheumatoid arthritis, systemic lupus erythematosus, and lupus nephritis.

Preferred is an embodiment of the present invention, wherein the inhibitor or pharmaceutical composition for use, as described herein, is selected from a small molecule, a peptide, an antibody or antigen-binding fragment thereof, an enzyme, and an aptamer.

Further preferred is an embodiment, wherein said autoimmune disease is an antiphospholipid syndrome (APS), in particular primary or secondary APS, primary Sjögren syndrome, rheumatoid arthritis, systemic lupus erythematosus, and lupus nephritis.

In the sixth aspect, the invention relates to a method of treating and/or preventing an autoimmune disease, such as, for example, antiphospholipid syndrome, in particular primary or secondary APS, primary Sjögren syndrome, rheumatoid arthritis, systemic lupus erythematosus, and lupus nephritis, in a subject, said method comprising administering to said subject in need of such treatment and/or prevention an effective amount of an inhibitor as identified and described herein or a pharmaceutical composition as described herein.

The terms "administering" or "administration" used herein cover enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcutaneous, subcuticular, intraarticular, subcapsular, subarachnoid, intraspinal, epidural and intrastern injection and infusion.

An "effective amount" as used herein, is an amount of the compound(s) or the pharmaceutical composition(s) as described herein that normalize the inflammatory state in the subject. The amount alleviates symptoms as found for the disease and/or condition, without being toxic to the subject. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range). However, doses below or above this exemplary range are envisioned, especially considering the aforementioned factors.

The terms "of the [present] invention", "in accordance with the invention", "according to the invention" and the like, as used herein are intended to refer to all aspects and embodiments of the invention described and/or claimed herein.

In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

All references, patents, and publications cited herein are hereby incorporated by reference in their entirety.

EXAMPLES

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

Example 1: EPCR-Dependent Signaling of aPL

Figure 1:
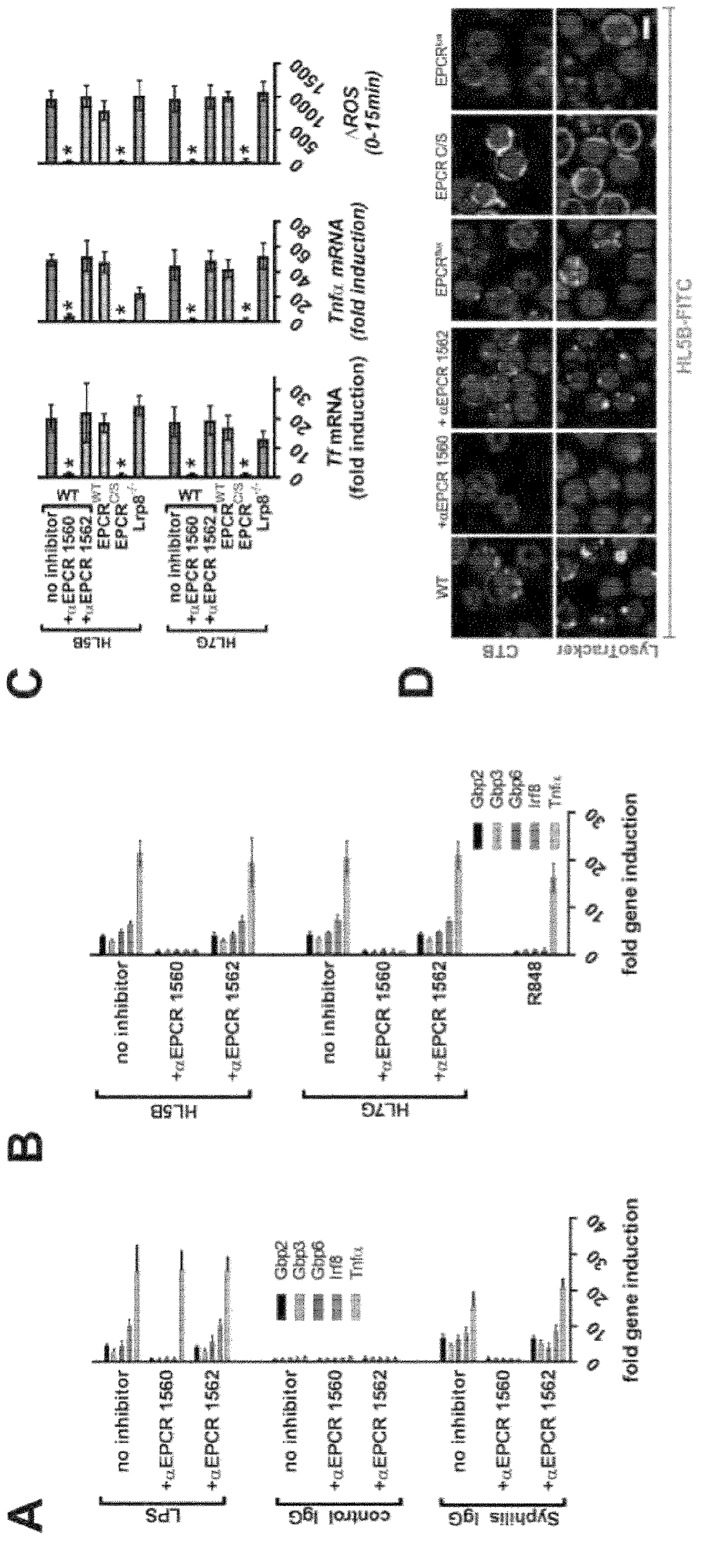
FIG. 1: shows that EPCR is the receptor for aPL (A) EPCR-dependent induction of IFN-regulated genes in monocytes by LPS and IgG from patients infected with *Treponema pallidum*. (B) Induction of IFN-regulated genes by aPL. (C) TF and Tnfα mRNA induction by aPL HL5B or HL7G stimulation of CD115+ splenocytes of indicated mice stimulated for 3 hours, as well as early ROS production; mean±SD, n=6; * $p<0.0001$; one-way ANOVA, Dunnett multiple-comparison test. (D) Live cell imaging of HL5B internalization in monocytes of indicated mouse strains. Bar=5 μm. (E) Live cell imaging of aPL HL5B Fab'2 or IgG colocalization with EPCR using non-inhibitory αEPCR 1489 in human MM1 cells. (F) Internalization of EPCR, FVIIa, and TF in MM1 cells stimulated for 15 minutes similarly required proteases and integrin trafficking. For quantification of internalization, surface staining was quenched with 0.4% trypan blue; mean±SD, n=6. * $p<0.0001$; one-way ANOVA, Dunnett multiple-comparison test compared to IgG control.
Figure 1:
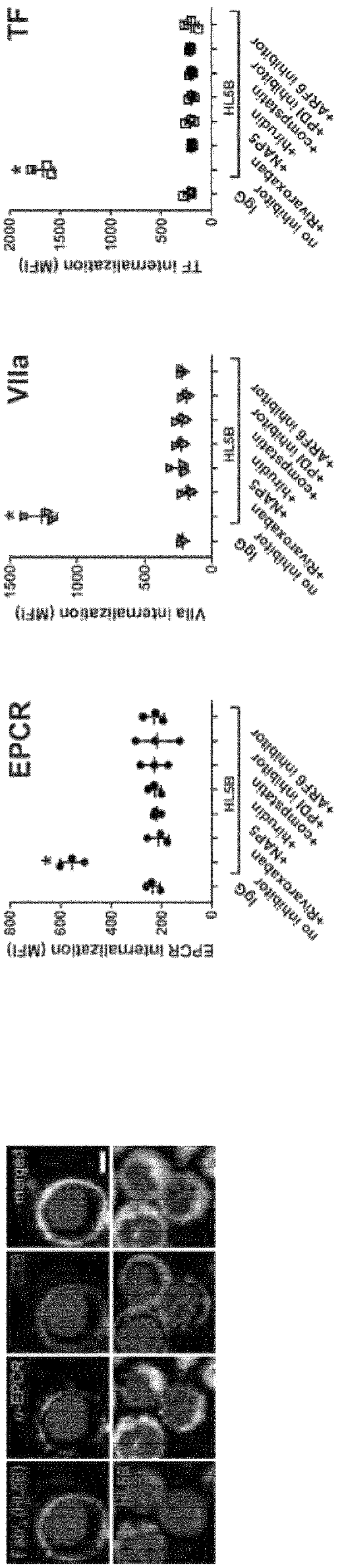

FXa generated by the coagulation initiator TF-FVIIa utilizes the endothelial protein C receptor (EPCR) for protease activated receptor (PAR) 2 cleavage that is specifically required for LPS-induced interferon (IFN) responses (15, 16). In accord with this pathway, inhibitory (αEPCR 1560), but not non-inhibitory (αEPCR 1562) antibodies to EPCR (FIG. 2A) blocked LPS induction of interferon-regulated host defense genes, but not the induction of pro-inflammatory TNFα in spleen-derived monocytes (FIG. 1A). Unexpectedly, lipid-reactive IgG fractions from patients with active syphilis (FIG. 1A) and well characterized lipid-reactive monoclonal aPL without (HLSB) or with (HL7G) β2GPI cross-reactivity (FIG. 1B) not only induced interferon-regulated genes, but also TNFα dependent on EPCR. Although aPL promote TNFα through amplification of Tlr7 signaling (9), the Tlr7 agonist R848 upregulated only TNFα, but not interferon-regulated genes (FIG. 1B), demonstrating that aPL engage EPCR in a novel pathway related to host defense.

Figure 2:
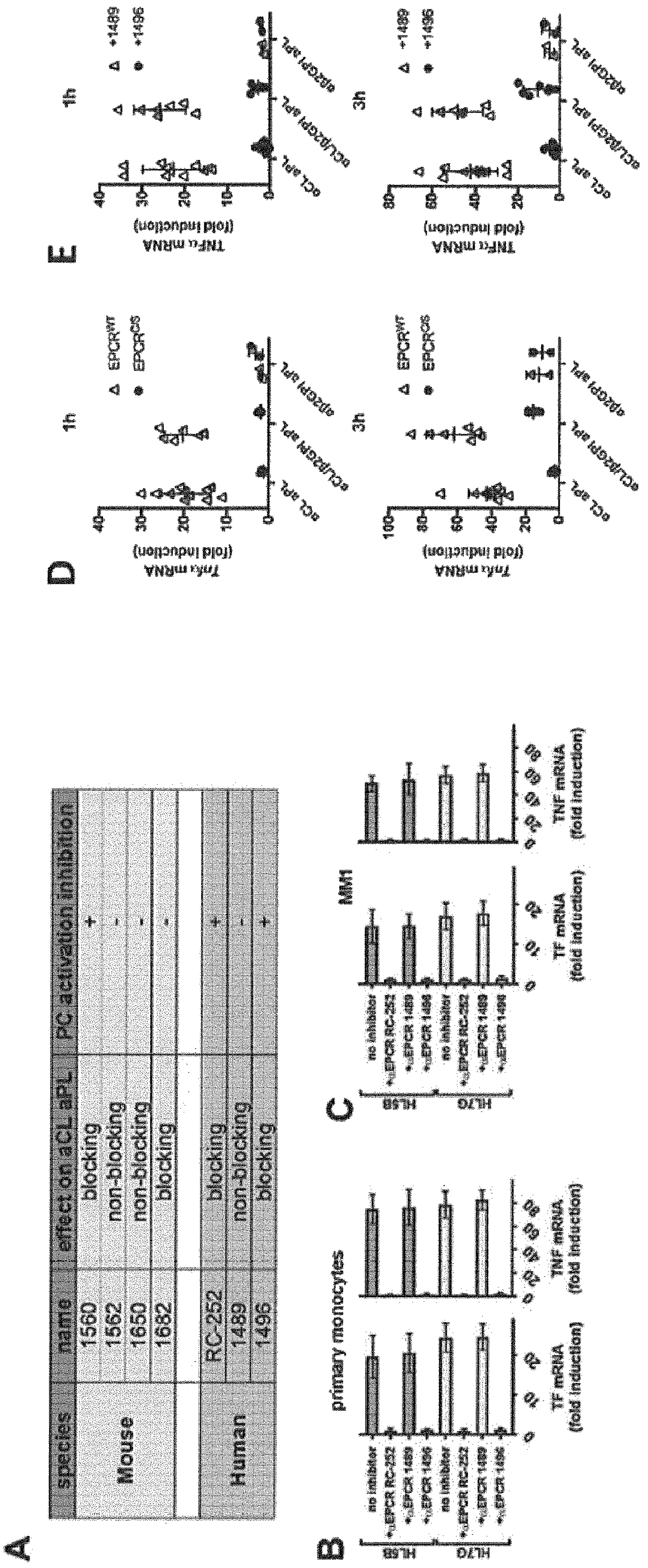
FIG. 2: shows that EPCR is required for aPL signaling. (A) Overview of functional properties of αEPCR against human and mouse EPCR. (B, C) TNF and TF induction in primary monocytes (B) and MM1 cells (C) stimulated for 3 h with HL5B or HL7G and pretreated for 15 minutes with anti-human EPCR antibodies; mean±SD, n=6. (D) CD115+ splenocytes of indicated mouse strains and (E) trophoblast cell induction of TNFα after 1 or 3 hours of stimulation with IgG isolated from APS patients (100 μg/ml) demonstrating cardiolipin reactivity alone (αCL), αβ2GP reactivity alone or dual reactivity. Human trophoblast cells were pretreated with either non-inhibitory αEPCR 1489 or inhibitory αEPCR 1496.

EPCR blockade similarly inhibited procoagulant and proinflammatory aPL responses in human monocytes (FIG. 2B, C). Function-blocking anti-mouse EPCR abolished broadly established aPL monocyte responses (FIG. 1D), i.e. TF, Tnfα and reactive oxygen species (ROS) production, that were independent of Lrp8 (FIG. 1D), a known co-receptor for EPCR-protein C (PC) signaling (17) and β2GPI-dependent aPL pathogenesis (12, 13). Importantly, elimination of the predicted EPCR intracellular palmitoylation acceptor Cys242 by knock-in mutagenesis to Ser in a novel mouse model, $EPCR^{C/S}$ mice, prevented aPL signaling, indicating that EPCR has a highly specific signaling function in aPL pathology.

Randomly selected patient IgG fractions representative of diagnostic reactivities found in general patient populations with APS (8, 11) were analyzed. Rare aPL IgG reactive with β2GPI alone (α-β2GPI; 2/20 patients) did not induce rapid proinflammatory responses, but signaling of lipid-reactive aPL IgG (defined by cardiolipin reactivity, α-CL) with (similar to monoclonal aPL HL7G; 7/20 patients) or without (similar to monoclonal aPL HL5B; 11/20 patients) β2GPI cross-reactivity was markedly reduced on mouse $EPCR^{C/S}$ monocytes (FIG. 2D) or human trophoblast cells in the presence of inhibitory αEPCR (FIG. 2E). These data showed not only that the vast majority of patient aPL preserved lipid-reactivity and EPCR-dependent signaling, but also a remarkable species preservation of this signaling mechanism in innate immune and embryonic cells.

Imaging demonstrated that aPL HL5B did not bind to EPCR-deficient ($EPCR^{low}$) monocytes (18) or cells blocked by the inhibitory αEPCR 1560, whereas the non-inhibitory αEPCR 1562 prevented neither binding nor aPL internalization (FIG. 1D). In contrast, aPL bound to $EPCR^{C/S}$ monocytes, but did not internalize (FIG. 1D). On human monocytes, aPL HL5B colocalized intracellularly with a non-inhibitory αEPCR after 15 minutes of stimulation, but there was only surface binding and no internalization when EPCR was engaged by Fab'2 fragments of the same aPL lacking complement-fixation (FIG. 1E). Complement is a known player in aPL pathologies (8, 19-21) and causes thiol-disulfide exchange and protein disulfide isomerase (PDI) mediated conformational changes in TF. This increases TF clotting activity (22) and enables coagulation-dependent TF-FVIIa trafficking in the ADP-ribosylation factor (ARF) 6 integrin pathway (23) to initiated aPL endosomal proinflammatory signaling (14). Inhibition of complement, PDI, and ARF6, as well as coagulation proteases FXa and thrombin, prevented not only TF-FVIIa, but also EPCR internalization (FIG. 1F), indicating that EPCR-bound aPL internalized together with the TF-FVIIa complex dependent on a cooperation of innate immune defense complement and coagulation pathways.

Example 2: EPCR Surface Presentation of Endosomal LBPA

Figure 3:
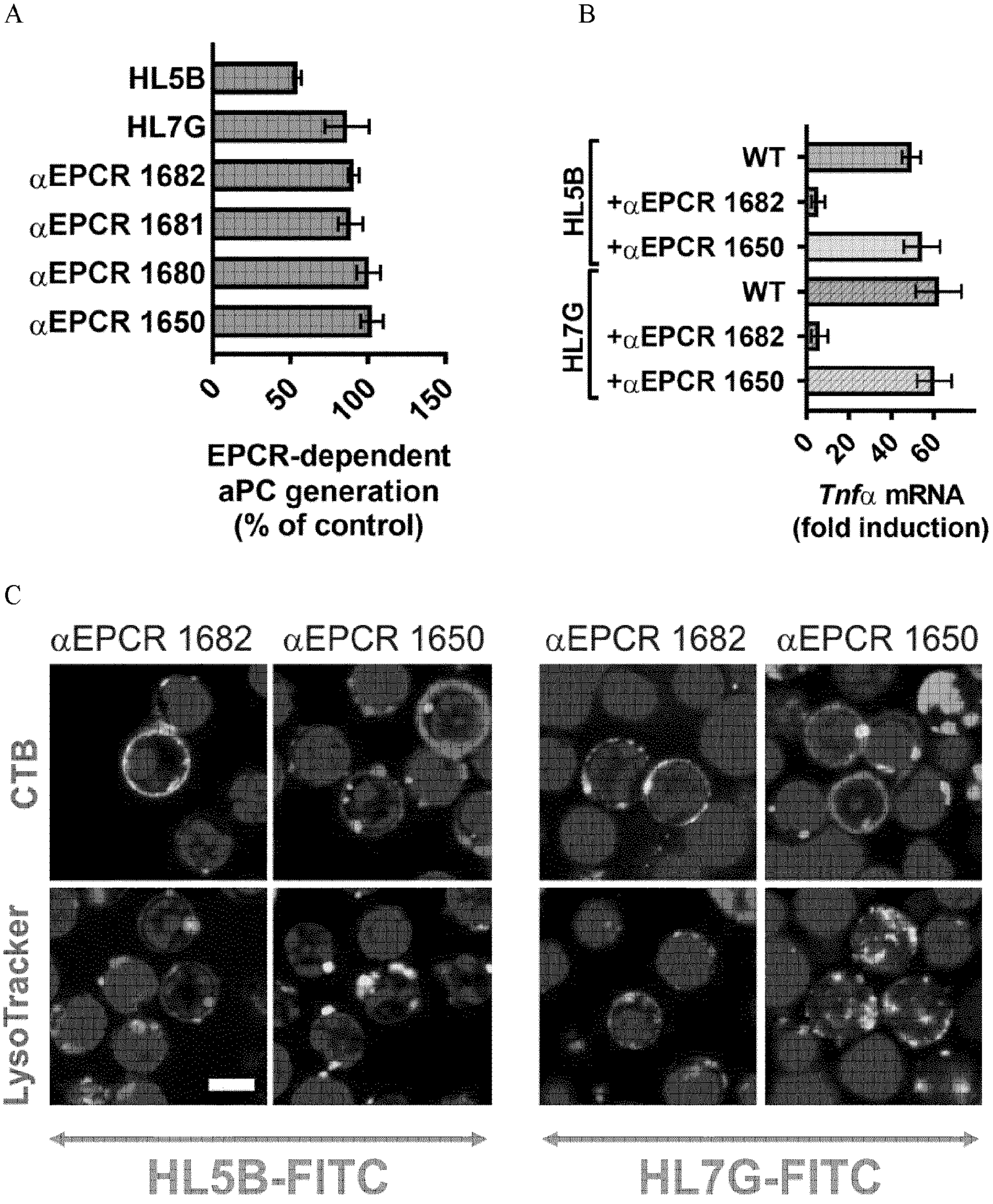
FIG. 3: shows that EPCR presents late endosomal lyso-bisphosphatidic acid (LBPA) on the cell surface. (A) Effect of aPL HL5B, aPL HL7G, and αEPCR antibodies on EPCR-dependent aPC generation on murine microvascular endothelial cells. (B) Effect of anti-mouse EPCR antibodies 1682 and 1650 on Tnfα mRNA induction by aPL HL5B and HL7G; mean±SD, n=6. * p<0.0001; one-way ANOVA, Dunnett multiple-comparison. (C) Effect of αEPCR on aPL HL5B and HL7G internalization in CD115+ splenocytes. Bar=5 μm. (D) Flow cytometry detection of FXa and EPCR on CD115+ spleen monocytes isolated from indicated mouse strains. (E) Effect of pre-treatment with 10 μM LBPA for 10 min on surface binding of αEPCR 1682 and αLBPA 6C4 on indicated monocytes; mean±SD, n=6. * p<0.003; multiple t-tests. (F) Competition of αEPCR 1650 and 1682 with binding of FITC-labelled anti-LBPA antibody 6C4 to mouse CD115+ splenocytes. (G) Competition of αLBPA 6C4 with binding of αEPCR 1682 to mouse monocytes. (H) Effect of LBPA, cardiolipin (CL), and phosphatidylserine (PS) (10 μM) on aPL HLSB signalling in $EPCR^{C/S}$ monocytes. Induction of TNF after 3 hours is shown; mean±SD, n=6. (I) LBPA loading of purified mouse or human sEPCR evidenced by faster mobility on native gels. (J) Surface plasmon resonance analysis of aPL HLSB binding to purified human sEPCR or sEPCR-LBPA. The affinity calculation was based on a monovalent binding model because no cooperative binding was evident.
Figure 3:
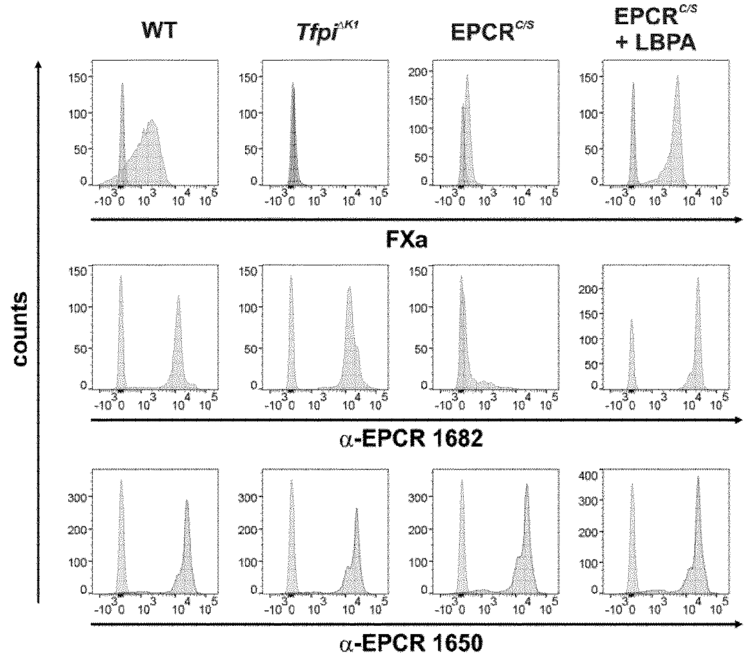
Figure 3:
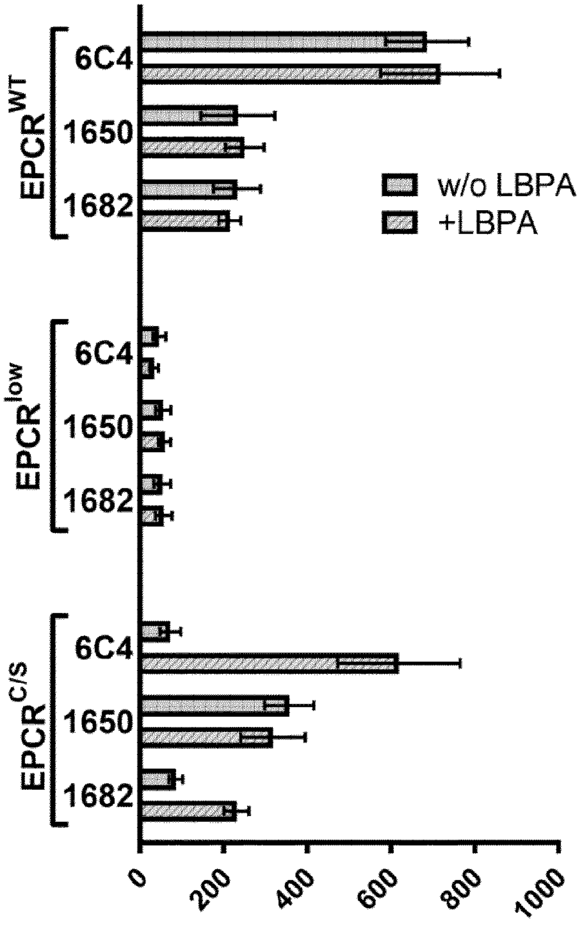
Figure 3:
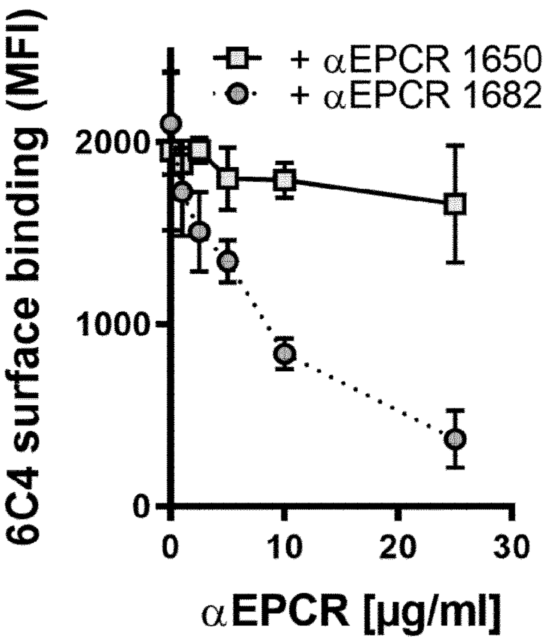
Figure 3:
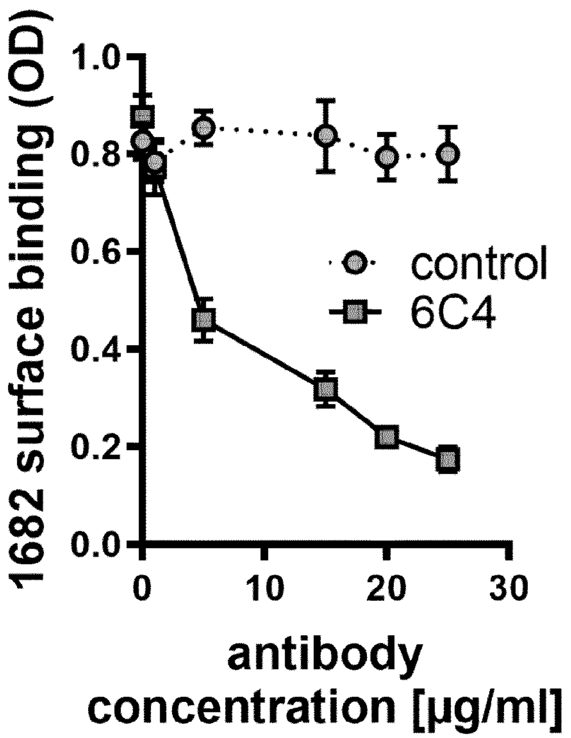
Figure 3:
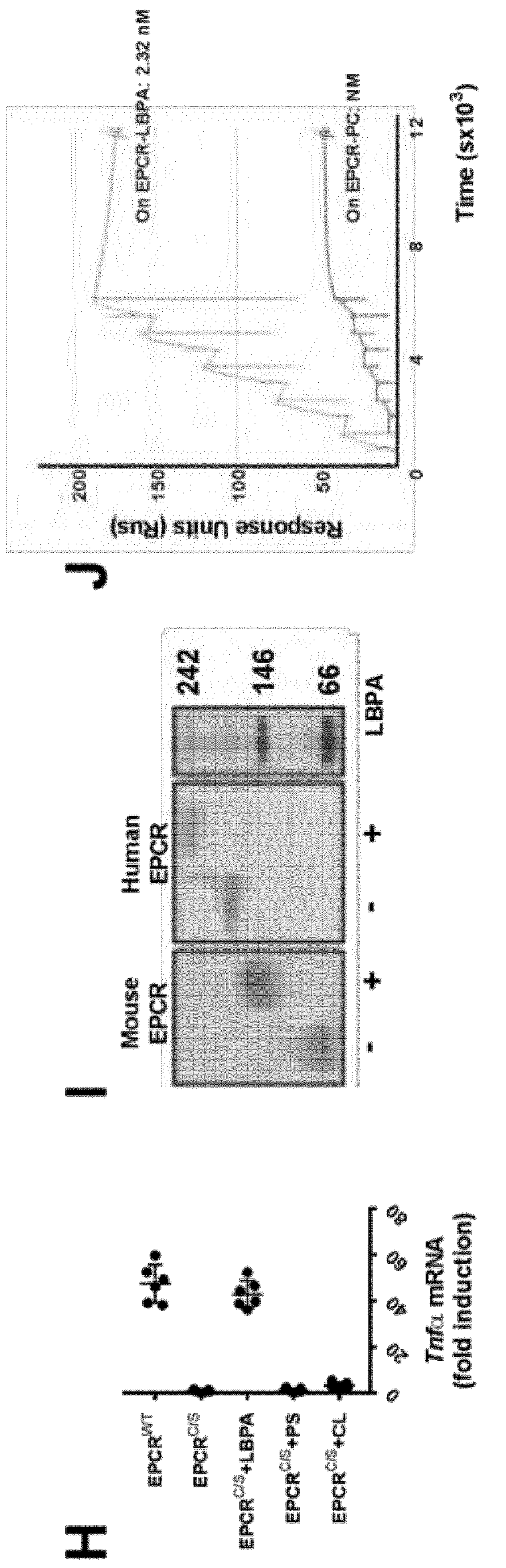

Certain aPL interfere with anticoagulation (24), but this feature was not common to all lipid-reactive prototypic aPL (FIG. 3A). Among anti-mouse EPCR antibodies that did not inhibit PC activation (FIG. 3A), a rare antibody, αEPCR 1682, with potent inhibition of aPL pro-inflammatory signaling (FIG. 2B) was identified and internalization without inhibiting aPL binding (FIG. 3C), indicating that αEPCR 1682 blocked a central pathway of aPL pathogenesis unrelated to coagulation factor or aPL binding to EPCR.

αEPCR 1682 surprisingly did not stain EPCR that was expressed at normal levels on monocytes from $EPCR^{C/S}$ mice (FIG. 3D). Since EPCR interacts with FXa (15) and FXa is crucial for TF pathway inhibitor (TFPI) complex formation and recycling (25), this was justified because altered EPCR trafficking in $EPCR^{C/S}$ mice prevented TF-FVIIa-FXa-TFPI complex formation and thus conformational changes required for αEPCR 1682 binding. Imaging surface bound FXa on TFPI-deficient TfpiΔK1 monocytes (14) showed that this complex indeed formed dependent on monocyte-synthesized TFPI and was absent in $EPCR^{C/S}$ cells. However, αEPCR 1682 stained TfpiΔK1 cells, excluding that αEPCR 1682 reactivity required FXa-EPCR interaction (FIG. 3D).

Because EPCR function is dependent on structurally bound lipid (26, 27), it was hypothesized that lipid exchange influenced EPCR antibody reactivity. The late endosomal lipid LBPA (lysobisphosphatidic acid, or bis(monoacylglycerol)phosphate (BMP)) is recognized by aPL after internalization (28) and EPCR and aPL trafficked through a common endo-lysosomal compartment (FIG. 1E). Supporting the possibility that LBPA replaced the structurally bound lipid of EPCR, non-permeabilized cells that express EPCR, but not EPCR-deficient or signaling-defective $EPCR^{C/S}$ cells, were stained with αLBPA 6C4 (FIG. 3E).

Importantly, simply adding LBPA to the culture medium of $EPCR^{C/S}$, but not EPCR-deficient cells restored cell surface αLBPA 6C4 and αEPCR 1682 staining (FIG. 3E) and promoted FXa surface localization (FIG. 3D). In addition, αEPCR 1682 specifically prevented binding of αLBPA 6C4 to mouse monocytes (FIG. 3F). Conversely, competition of αLBPA 6C4 with αEPCR 1682 binding showed that αEPCR 1682 recognized LBPA-loaded EPCR (FIG. 3G). Remarkably, only supplementation with LBPA, but not with the commonly assumed aPL ligand cardiolipin (CL) or the negatively charged procoagulant phosphatidylserine (PS) restored aPL pro-inflammatory signaling of $EPCR^{C/S}$ cells (FIG. 3H).

Exposure of purified insect cell-expressed human or mouse soluble EPCR (sEPCR) (15) to LPBA yielded a re-purified protein with a marked shift in mobility on native gels, demonstrating lipid exchange with LBPA (FIG. 3I). Purified human sEPCR showed tight binding of aPL HL5B with LBPA-loaded EPCR, whereas binding affinity could not be quantified by surface plasmon resonance with unmodified sEPCR (FIG. 3J). Thus, EPCR-LBPA is the antigenic target recognized by aPL.

Figure 4:
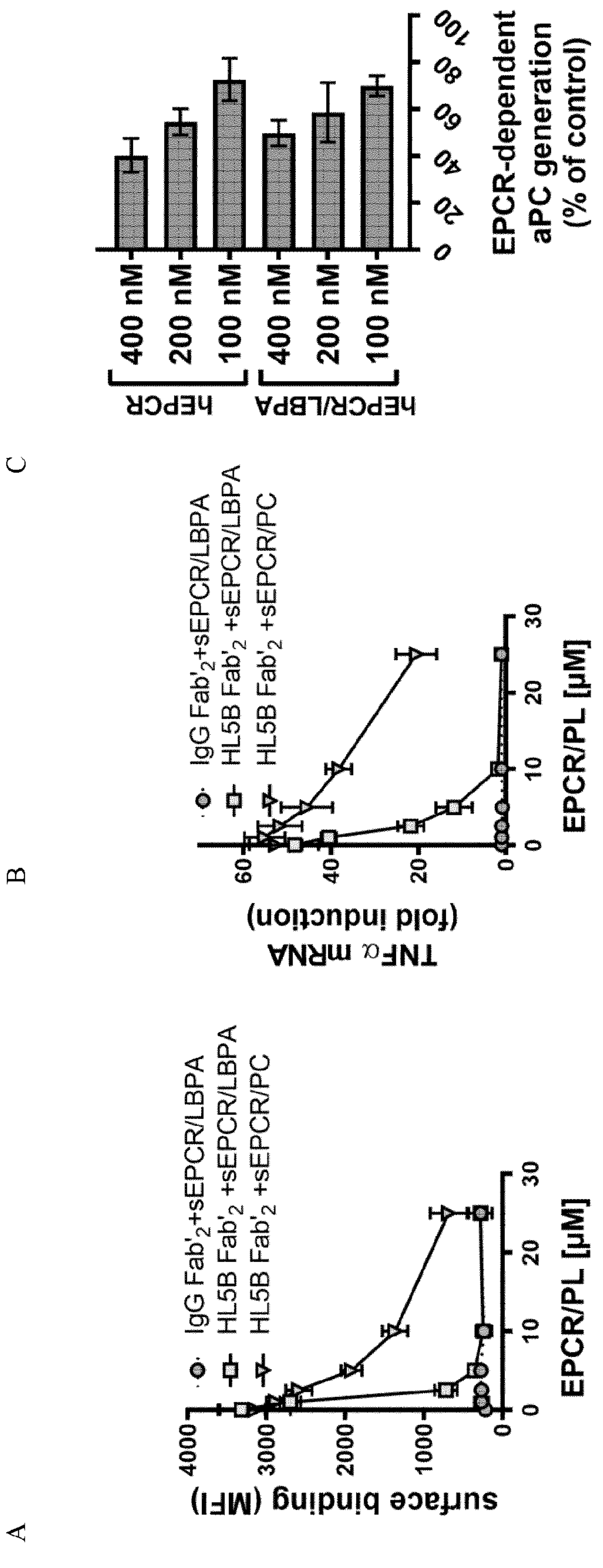
FIG. 4: shows the effect of EPCR LBPA loading on aPL interaction. (A) Competition by sEPCR either loaded with LBPA or unmodified with binding of FITC-labeled HLSB Fab'2 fragments or control to mouse monocytes by flow cytometry. (B) LBPA-loaded EPCR is a more potent inhibitor than unmodified EPCR in blocking aPL HLSB signaling. (C) LBPA loading of human sEPCR does not alter competition of sEPCR with aPC generation on mouse endothelial cells. (D) Binding of HLSB to CHO cell control and CHO cells expressing mouse EPCR (mEPCR). Cells were either untreated or pre-incubated for 30 min with 10 μM LBPA, mean±SD, n=6. (E) Binding of anti-β2GPI aPL rJGG9 or control IgG to moue EPCR transfected CHO measured in a fluorescence microplate reader, mean±SD, n=3. (F) Binding of aPL HLSB, aPL HL7G or control IgG to mouse (mEPCR) or human (hEPCR) transfected CHO cells. Cells were loaded with 10 μM LBPA for 30 minutes before staining. (G) Binding of aPL HLSB (left panel) or HL7G (right panel) to LBPA-loaded mouse EPCR after preincubation for 15 minutes with different concentrations of purified sEPCR either unmodified or loaded with LBPA; mean±SD, n=6. (H) Dose response curve of HLSB and HL7G triggered PS exposure measured by annexin 5 surface staining.
Figure 4:
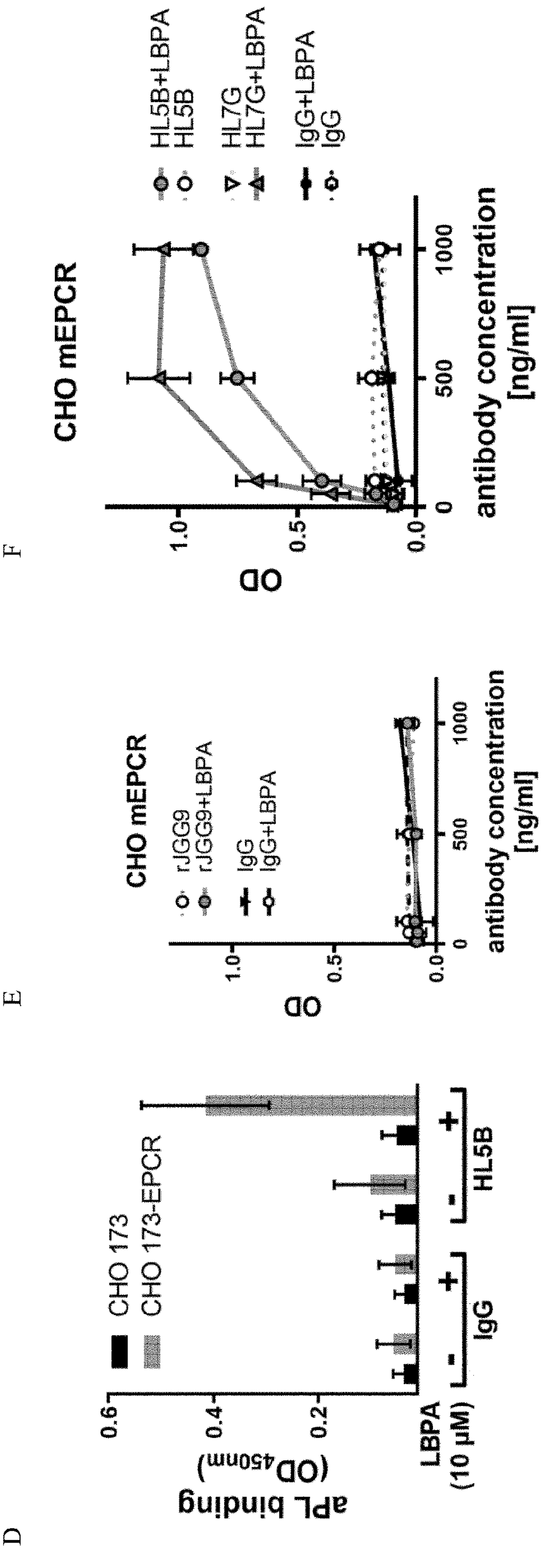
Figure 4:
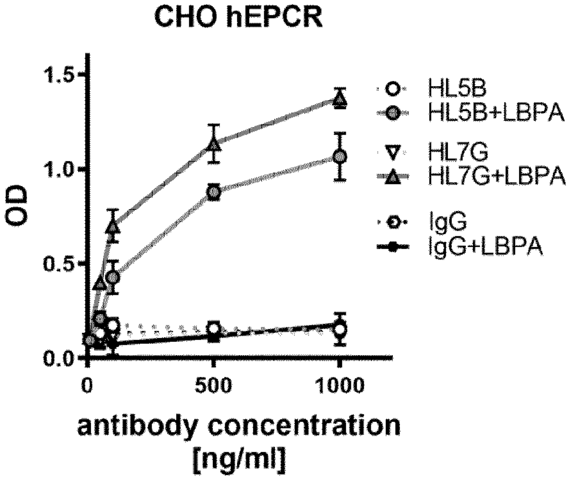
Figure 4:
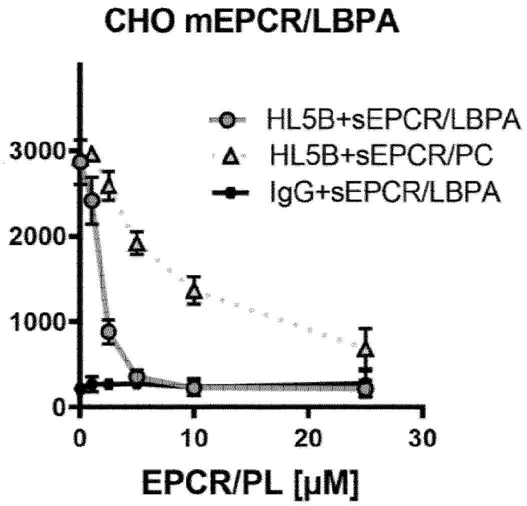
Figure 4:
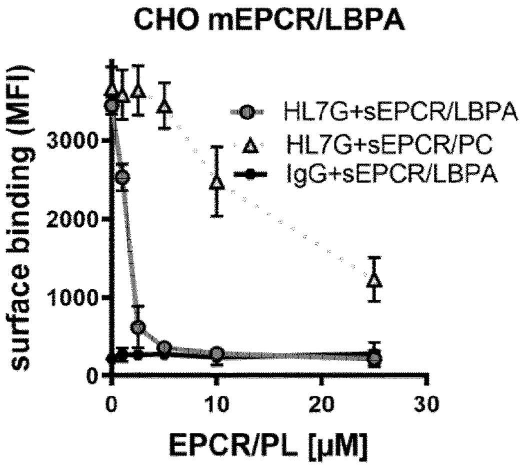
Figure 4:
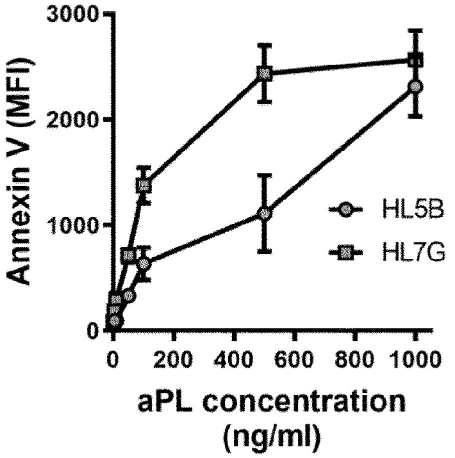

Competition experiments confirmed the high affinity of aPL HL5B for LBPA-loaded sEPCR (FIG. 4A, B), while LBPA loading did not increase the potency of EPCR to inhibit PC activation (FIG. 4C). Only lipid-reactive, but not β2GPI-specific aPL recognized mouse or human EPCR loaded with LBPA (FIG. 4D-E). Cellular binding assays (FIG. 4F), competition experiments (FIG. 4G) and a monocyte activation readout (FIG. 4H) indicated a somewhat higher affinity of β2GPI cross-reactive aPL HL7G in comparison to lipid-selective aPL HLSB. Thus, acquisition of protein-reactivity during evolution of aPL appears to be compatible with affinity maturation for the pathogenic target EPCR-LBPA; this finding may be of importance for interpreting clinical correlations of β2GPI cross-reactivity with APS severity.

Example 3: EPCR-LBPA is the Target for aPL-Induced Thrombosis

Figure 5:
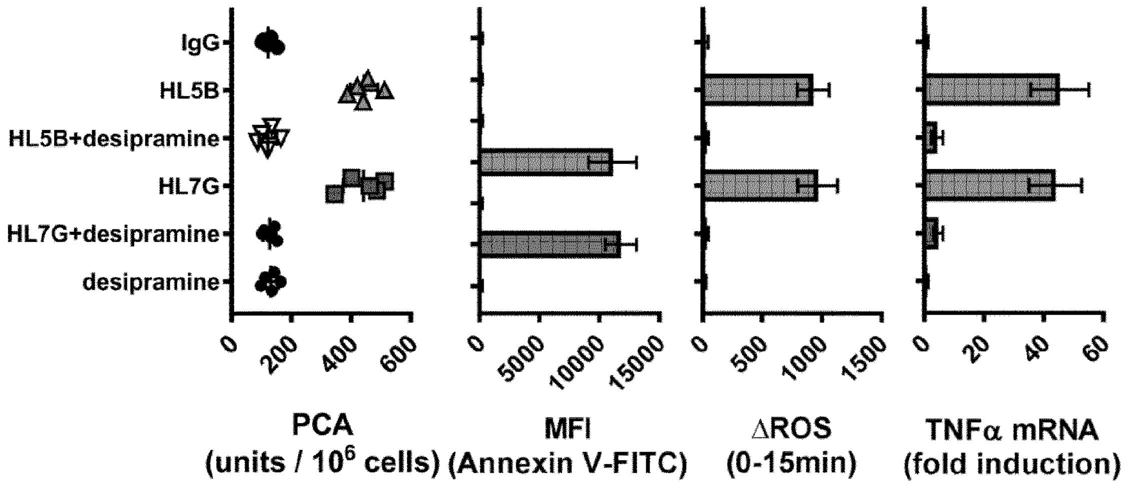
FIG. 5: shows that aPL promote EPCR-LBPA activation of cell surface acidic sphingomyelinase and thrombosis. (A) aPL-mediated TF activation, PS exposure measured by annexin 5 staining, ROS production and TNFα induction as well as (B) aPL internalization in MM1 cells was blocked by sphingomyelinase inhibitor desipramine. Bar=5 μm. (C) aPL-induced ASM activity in MM1 cells is blocked by inhibitors of FXa, thrombin, and PAR1 cleavage. (D) Live cell imaging of surface ASM exposure in MM1 cells after 30 minutes of stimulation with Fab'2 aPL HLSB. Bar=5 μm. (E) ASM activity in unstimulated cell lysates after addition of sEPCR-LBPA (2.504) is blocked by αEPCR 1682. For all ASM activity assays: mean±SD, n=3. * p<0.0003; one-way ANOVA, Dunnett multiple-comparison test. (F) HLSB-induced thrombosis analyzed in the flow restricted vena cava inferior of WT mice treated with the indicated αEPCR antibodies. (G, H) Thrombosis induction by dual reactive aPL HL7G in the indicated mouse strains or WT mice in presence of indicated αEPCR. (F-H) Quantification of thrombus size 3 hours after aPL injection; median, interquartile range, and range; n=6-11; * p <0.004; one-way ANOVA, Dunnett multiple-comparison test compared to αEPCR 1650. (I, J) Thrombosis induction by aPL HLSB (I) or IgG isolated from age-matched 16 weeks old lupus-prone MRL/lpr and MRL control mice (J) in the indicated mouse strains. Quantification of thrombus size 3 hours after aPL injection; median, interquartile range, and range; (I) n=6-10; * p=0.001; unpaired t-test. (J) n=5; * p=0.0025; two-way ANOVA, Sidak's multiple comparisons test.
Figure 5:
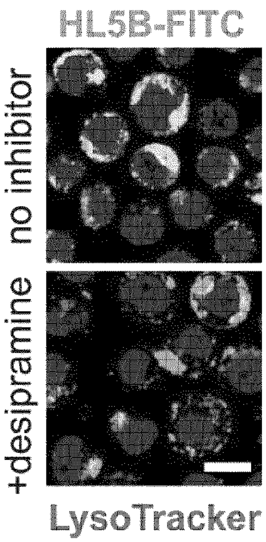
Figure 5:
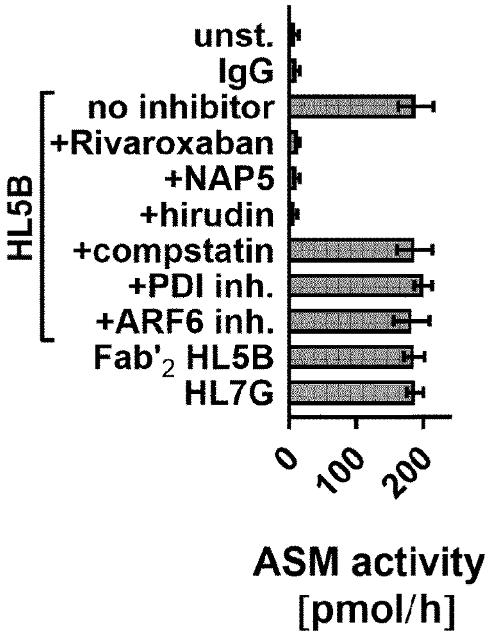
Figure 5:
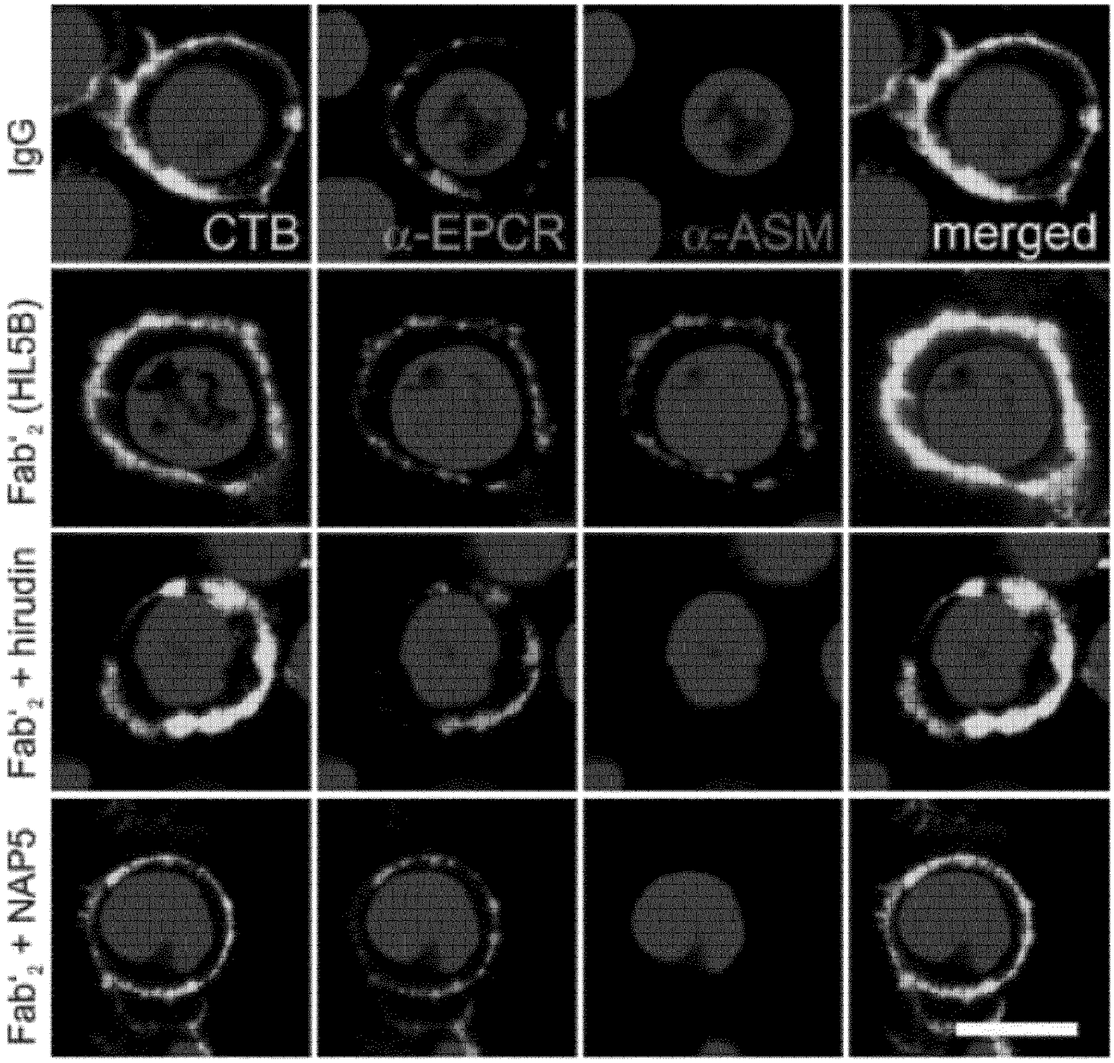
Figure 5:
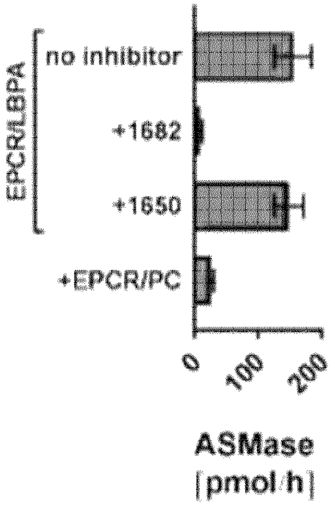
Figure 5:
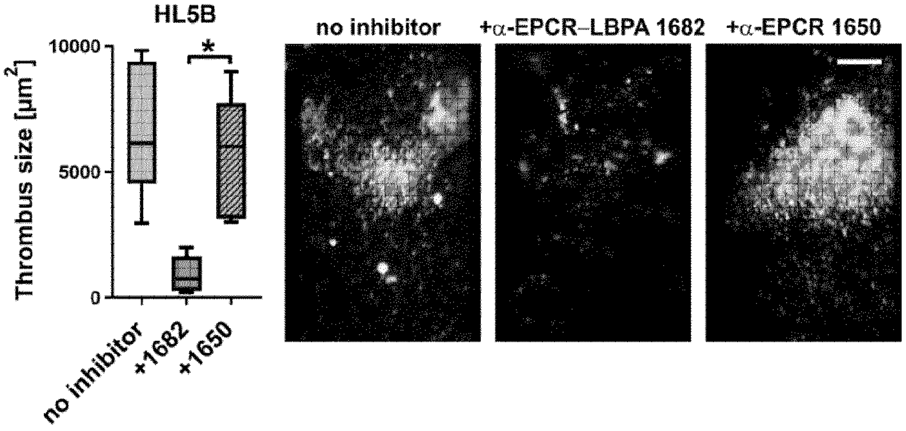
Figure 5:
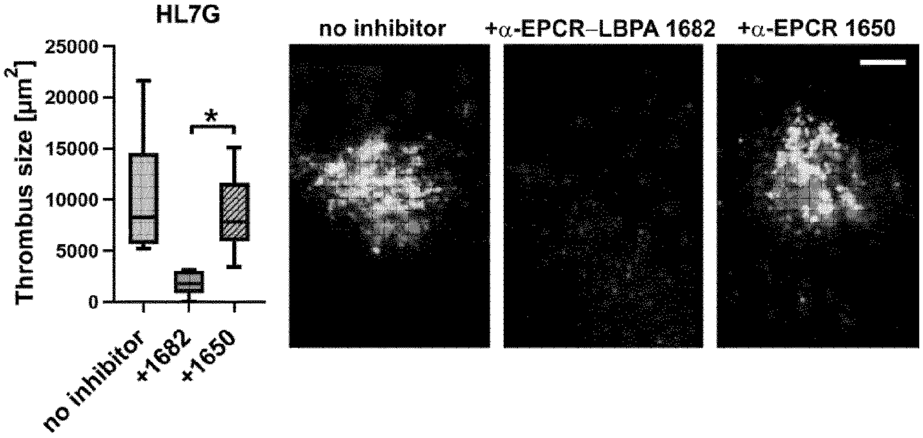
Figure 5:
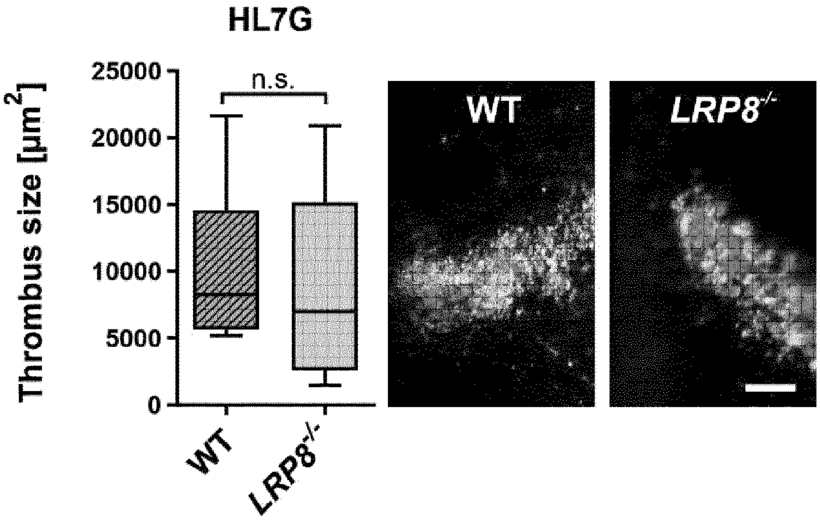
Figure 5:
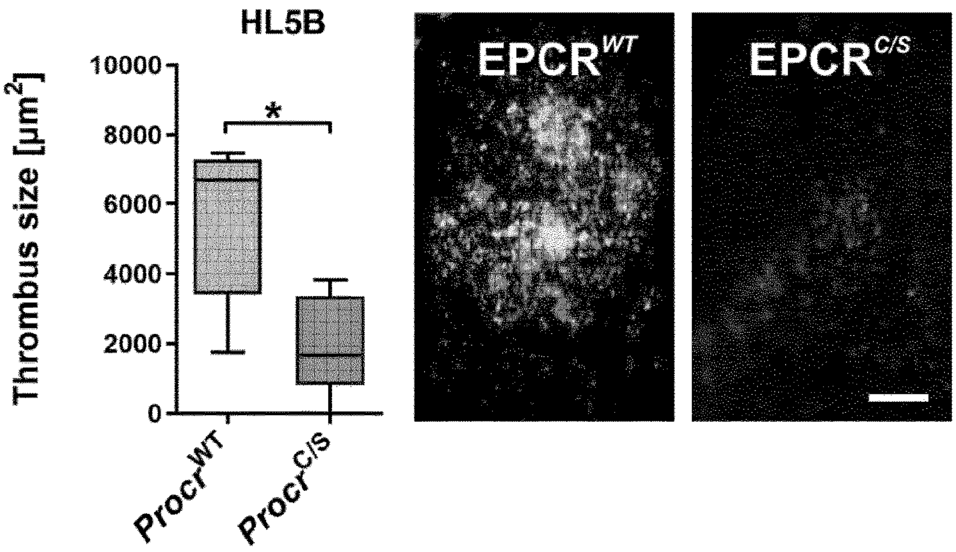
Figure 5:
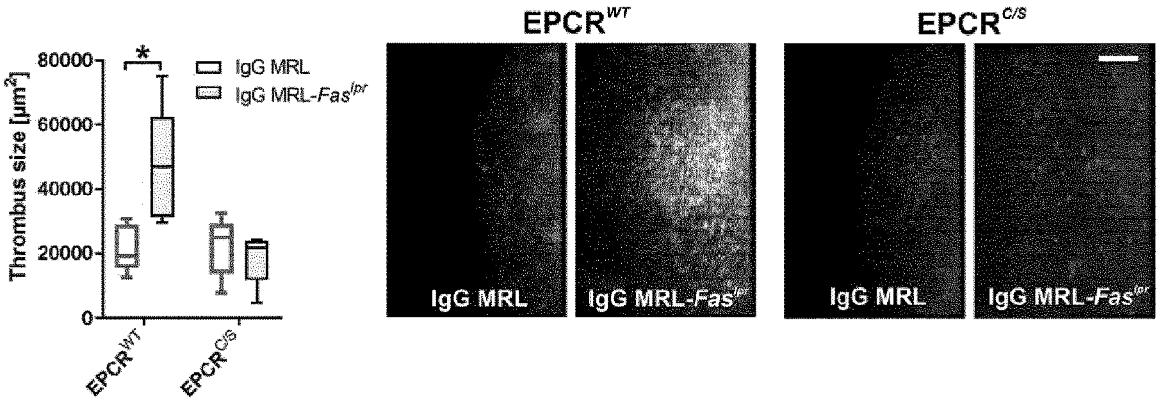
Figure 6:
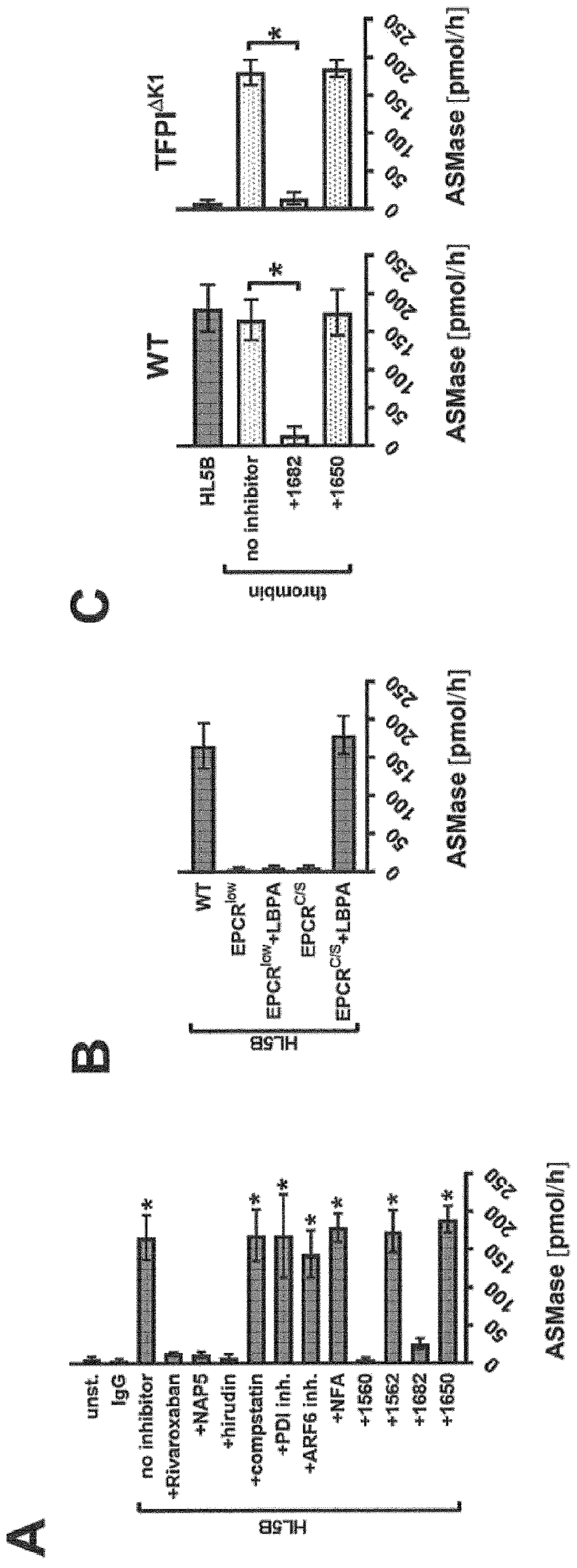
FIG. 6: shows that aPL promote EPCR-LBPA activation of cell surface acidic sphingomyelinase. (A) WT CD115+ spleen monocyte induction of ASM activity after 15 minutes aPL HLSB stimulation with the indicated inhibitors. (B) LBPA (10 μM) loading of $EPCR^{C/S}$ cells enabled ASM activation in CD115+ monocytes stimulated with HLSB. (C) aPL HLSB did not activate ASM in TfpiΔK1 cells, but thrombin (1 U/ml) activation of ASM in WT and TfpiΔK1 cells was blocked by αEPCR 1682, but not αEPCR 1650.

It remained unclear why blockade of surface lipid-presentation by αEPCR-LBPA 1682 was sufficient to inhibit aPL signaling without preventing aPL binding. Because aPL rapidly induced procoagulant phosphatidylserine exposure (FIG. 4H), a process amplified by acidic sphingomyelinase (ASM) (29), ASM was blocked with desipramine and ASM was considered necessary for aPL pathogenic signaling (FIG. 5A) and aPL internalization (FIG. 5B). Various agonists, including thrombin, induce ASM cell surface translocation (30-32). Within 15 minutes, aPL maximally stimulated ASM activity in human monocytic cells dependent on FXa and thrombin-dependent PAR1 cleavage (FIG. 5C). However, ASM activity was not blocked by inhibitors of complement, PDI, or ARF6, indicating that ASM activation solely required coagulation activation, but not TF-FVIIa internalization. This pathway of ASM activation was conserved in the mouse (FIG. 6A). Importantly, Fab'2 of aPL HLSB also induced ASM activity and promoted thrombin-dependent appearance of ASM on the cell surface (FIG. 5D), confirming that ASM activation is an early event that precedes aPL internalization and endosomal trafficking.

ASM requires LBPA for activity (33). ASM activation was not only prevented by antibodies preventing aPL binding to EPCR, but also by αEPCR-LBPA 1682 (FIG. 6A). In a series of experiments, it was further showed that EPCR-LBPA directly activated cell surface ASM. Extracellular addition of LBPA to $EPCR^{C/S}$ but not to EPCR-deficient monocytes restored ASM activation by aPL (FIG. 6B). Thrombin stimulation to induce ASM surface expression was sufficient to trigger ASM activation that was blocked by extracellular addition of αEPCR-LBPA 1682 (FIG. 6C). TfpiΔK1 cells expressed LBPA-loaded EPCR (FIG. 3D), but lack surface FXa to trigger thrombin generation. ASM activation in these cells was not induced by aPL, but by thrombin in dependence of EPCR-LBPA (FIG. 6C). Addition of purified EPCR-LBPA, but not unmodified EPCR to cell lysates of unstimulated cells also efficiently induced ASM activity and this effect was blocked specifically by αEPCR-LBPA 1682 (FIG. 5E). Thus, coagulation-induced PAR1 signaling translocates ASM for cell surface activation by EPCR-LBPA. In turn, ASM modification of surface lipid modification is required for endosomal trafficking and signaling of EPCR-bound aPL.

Given that monocytes cause thrombosis (34), first the unique properties of mouse monoclonal αEPCR 1650 and 1682 were exploited, which lacked interference with the anti-coagulant PC pathway, while differentially regulating aPL pathogenic signaling (FIG. 3A, B). Thrombosis was markedly attenuated by αEPCR-LBPA 1682, but not by the non-inhibitory αEPCR 1650 (FIG. 5F). Similarly, Lrp8-independent thrombosis induction by the dual-reactive aPL HL7G was blocked specifically by αEPCR-LBPA 1682 (FIG. 5G, H).

Importantly, thrombosis induction by aPL HL5B was markedly reduced in $EPCR^{C/S}$ as compared to strain-matched WT controls (FIG. 5I). In order to assess the broader implications of these finding for autoimmune pathologies, IgG fractions from 16 weeks old prothrombotic lupus-prone MRL-lpr mice (35) and age-matched lupus-free MRL control mice were isolated. Thrombosis induction by pathogenic IgG was reversed when injected into $EPCR^{C/S}$ mice to levels seen with IgG isolated from control mice (FIG. 5J), confirming the central role of the identified signaling target for thrombosis associated with autoimmune disease.

Example 4: EPCR Pathogenic Signaling in Fetal Loss

Figure 7:
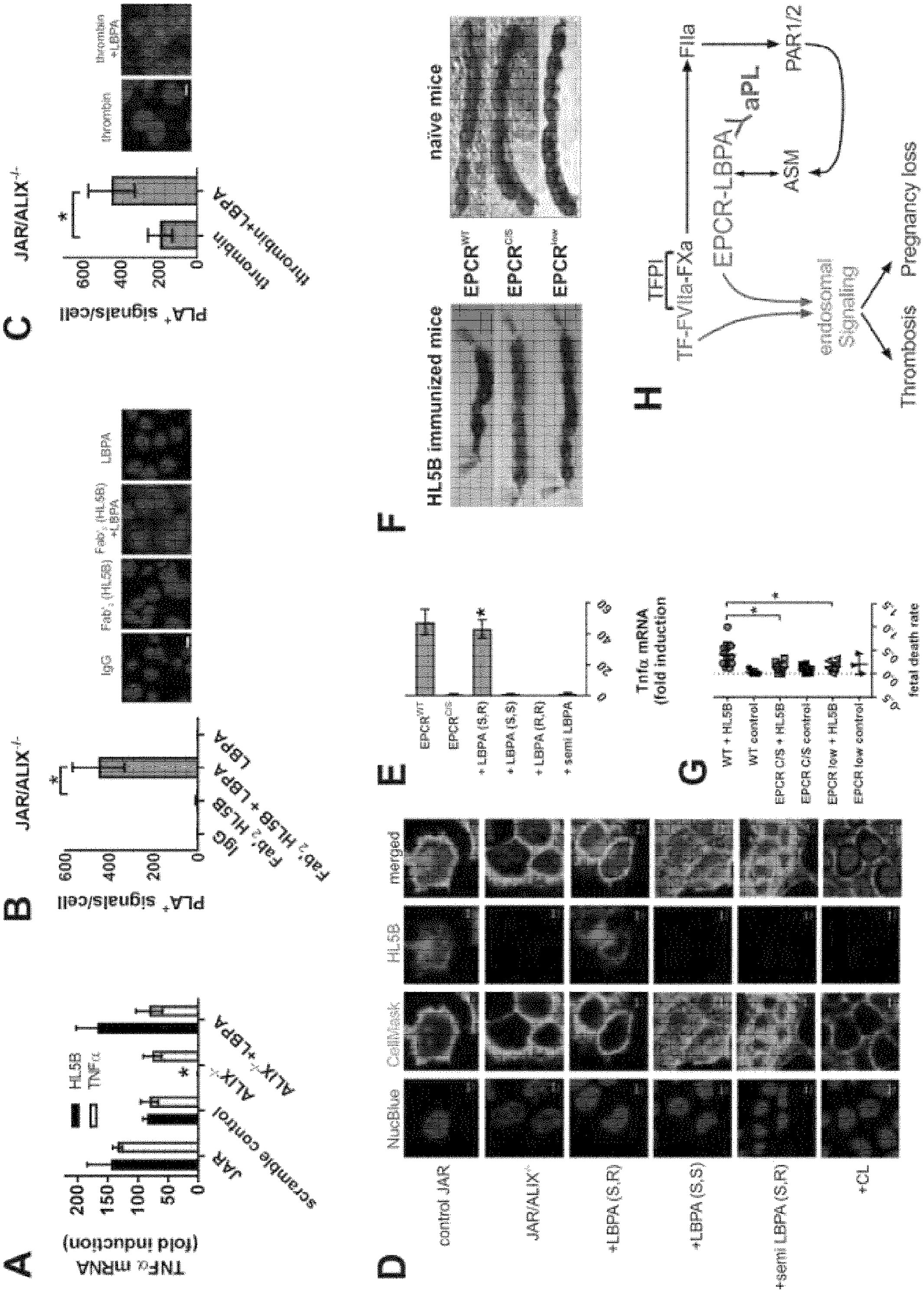
FIG. 7: shows that aPL-EPCR signalling promotes foetal loss. (A) TNFα mRNA induction after 2 hours by HLSB is prevented in Alix-deficient trophoblast cells; mean±SD, n=6. * p<0.0001; t-test following Shapiro-Wilk test for normal distribution. (B, C) Proximity ligation assays (PLA) for ASM and EPCR on scrambled control JARs or ALIX−/− cells after 10 minutes of stimulation with HLSB (B) or thrombin (C) with or without LBPA loading. Bar=25 μm. (D) aPL internalization in ALIX deficient JAR cells and signalling in $EPCR^{C/S}$ monocytes (E) was restored by adding 10 μM LBPA (S,R) but not by other phospholipids. (F, G) Pregnancy loss was scored at day 15.5 p.c. after injection of aPL HLSB on days 8 and 12. * p<0.02; one-way ANOVA, Dunnett multiple-comparison test. (H) Schematic representation of aPL signalling leading to thrombosis or pregnancy complications.
Figure 8:
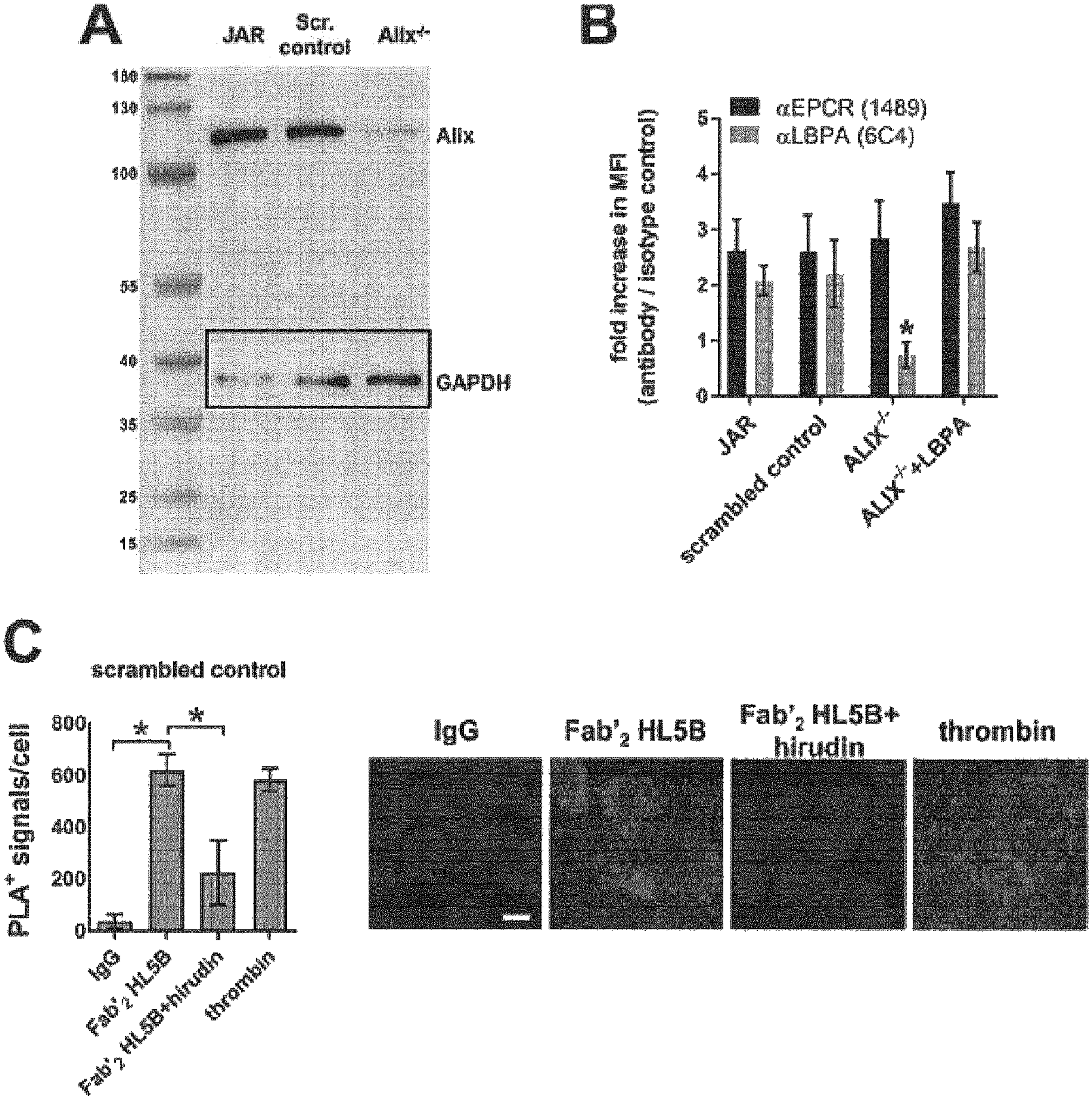
FIG. 8: shows that EPCR-LPBA is required for aPL signalling in trophoblast cells. (A) WB analysis of ALIX deficient JAR cells. (B) Loss of LBPA surface expression in ALIX knockdown trophoblast (JAR) cells expressing EPCR. Cells were stained with FITC labelled αEPCR or αLBPA antibodies and antibody surface binding was detected using a microplate fluorometer. (C) Proximity ligation assays (PLA) for ASM and EPCR on scrambled control JAR cells after 10 minutes of stimulation with thrombin and HL5B with or without thrombon inhibitor hirudin. Bar=25 μm.

The importance of this pathway in human trophoblast cells by knock-down of ALIX (FIG. 8A) was evaluated, which is required for normal lysosomal functioning. ALIX knock-down diminished LBPA cell surface presentation, but not EPCR expression (FIG. 8B) and abolished aPL-induced, but not TNFα-induced proinflammatory effects. However, supplementing extracellular LBPA restored aPL signaling (FIG. 7A). In support of a direct interaction between ASM and EPCR, proximity ligation assays (PLA) showed that EPCR and ASM colocalized after stimulation with thrombin or aPL Fab'2 HLSB (FIG. 8C) but not in hirudin-treated or $ALIX^{-/-}$ cells without additional of LBPA (FIG. 7B). In addition, thrombin recruitment of ASM showed increased proximity ligation with EPCR in $ALIX^{-/-}$ cells after exposure to LBPA (FIG. 7C). Thus, EPCR-LBPA directly interacts with cell surface ASM to stimulate its activity.

Human $ALIX^{-/-}$ trophoblast cells and murine $EPCR^{C/S}$ monocytes provided tools to compare the species conservation of lipid presentation by EPCR. Only addition of S/R 18:1 LBPA and R/R 18:1 LBPA, but not S/S 18:1 LBPA or semi-S/R LBPA restored aPL HL5B binding to $ALIX^{-/-}$ trophoblast cells (FIG. 7D) or signaling in $EPCR^{C/S}$ monocytes (FIG. 7E). Thus, human and mouse EPCR present LBPA with the same selectivity, providing an explanation for the remarkable species cross-reactivity of pathogenic aPL.

Further, the role of EPCR in a mouse model of aPL-induced pregnancy loss was analyzed. Although EPCR plays a pivotal role in maintaining embryonic trophoblast function and survival (36), no significant embryo loss in $EPCR^{C/S}$ mice or $EPCR^{low}$ mice relative to WT controls (FIG. 7F, G) was found. However, EPCR signaling-deficient mice were protected from fetal loss induced by lipid-reactive aPL HL5B. These experiments show that the newly identified aPL-EPCR signaling pathway is crucial for the major pathologies of APS, i.e. thrombosis and pregnancy loss, induced by lipid-reactive, as well as β2GPI-cross-reactive aPL in vivo (FIG. 7H).

Example 5: Development of Autoimmunity by aPL-Induced Interferon Signalling

Figure 9:
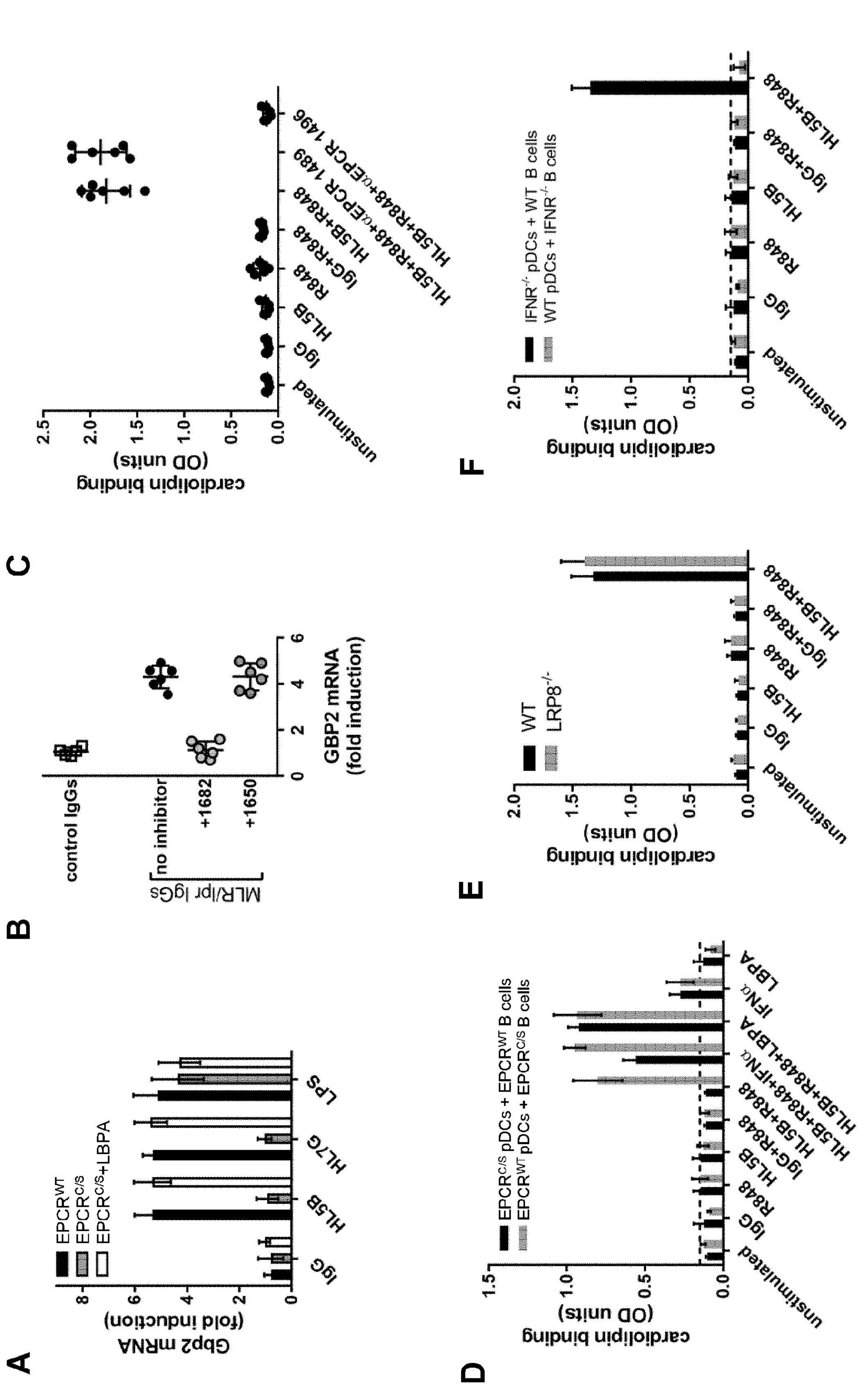
FIG. 9: shows that EPCR is required for aPL interferon signalling and the expansion of B cells producing lipid-reactive aPL. (A) Gbp2 mRNA induction after 1 hour stimulation with HL5B, HL7G, or LPS (100 ng/ml) in $EPCR^{C/S}$ or WT monocytes with or without addition of LBPA. (B) WT monocytes were stimulated for 1 hour with IgG isolated from MRL/lpr lupus-prone or control MRL mice in the presence of the indicated antibodies to EPCR. (C) Human monocyte-derived DC were co-cultured with B cells in the presence of TLR7/8 agonist R848 and aPL HL5B with the indicated antibodies to human EPCR. Anti-cardiolipin titers were determined after 10 days. (D-F) Co-cultures of isolated spleen plasmacytoid dendritic cells (pDC) and B cells from the indicated mouse strains were co-cultured with Tlr7 agonist R848 and aPL HL5B for 10 days, followed by determination of anti-cardiolipin titers. $IFNR^{-/-}$, type I interferon receptor deficient mice.

Further, it was investigated whether the identified target for lipid-reactive aPL contributes to the development of autoimmunity. Upregulation of interferon responses in circulating immune cells are linked to the development of APS (38, 39). Induction of interferon-regulated genes (e.g. IRF8, GBP2, GBP6) by lipid-reactive aPL, but not by LPS, was abolished in $EPCR^{C/S}$ monocytes and, as shown for GBP2, LBPA addition restored interferon responses (FIG. 9A). In addition, IgG isolated from MRL/lpr lupus erythematosus mice, but not MRL control mice induced interferon responses dependent on EPCR-LPBA in monocytes (FIG. 9B).

Co-cultures of human plasmacytoid dendritic cells (pDC) with B cells in the presence of an agonist for Tlr7, which contributes to auto-immunity in lupus erythematosus (40, 41), required addition of aPL to promote the production of cardiolipin-reactive antibodies (FIG. 9C). Under these conditions, a function-blocking (αEPCR1496), but not non-inhibitory (αEPCR1489) antibody to EPCR prevented the development of lipid-reactive antibodies (FIG. 9C), suggesting that EPCR-dependent interferon signaling drives autoimmune antibody responses.

Supporting this conclusion, anti-cardiolipin antibody production was absent when mouse pDC, but not B cells, were isolated from $EPCR^{C/S}$ mice (FIG. 9D). Addition of LBPA or interferon α restored the expansion of anti-cardiolipin producing B cells in co-cultures with aPL signaling-deficient $EPCR^{C/S}$ pDC (FIG. 9D). In contrast, cells deficient in LRP8, the receptor for β2GPI, produced anti-cardiolipin antibodies normally in response to co-stimulation of aPL and Tlr7 agonist (FIG. 9E). Appearance of lipid-reactive antibodies required type I IFN receptor expression by B cells, but not pDC (FIG. 9F), demonstrating that aPL induced pDC interferon production to stimulate B cell responses.

Figure 10:
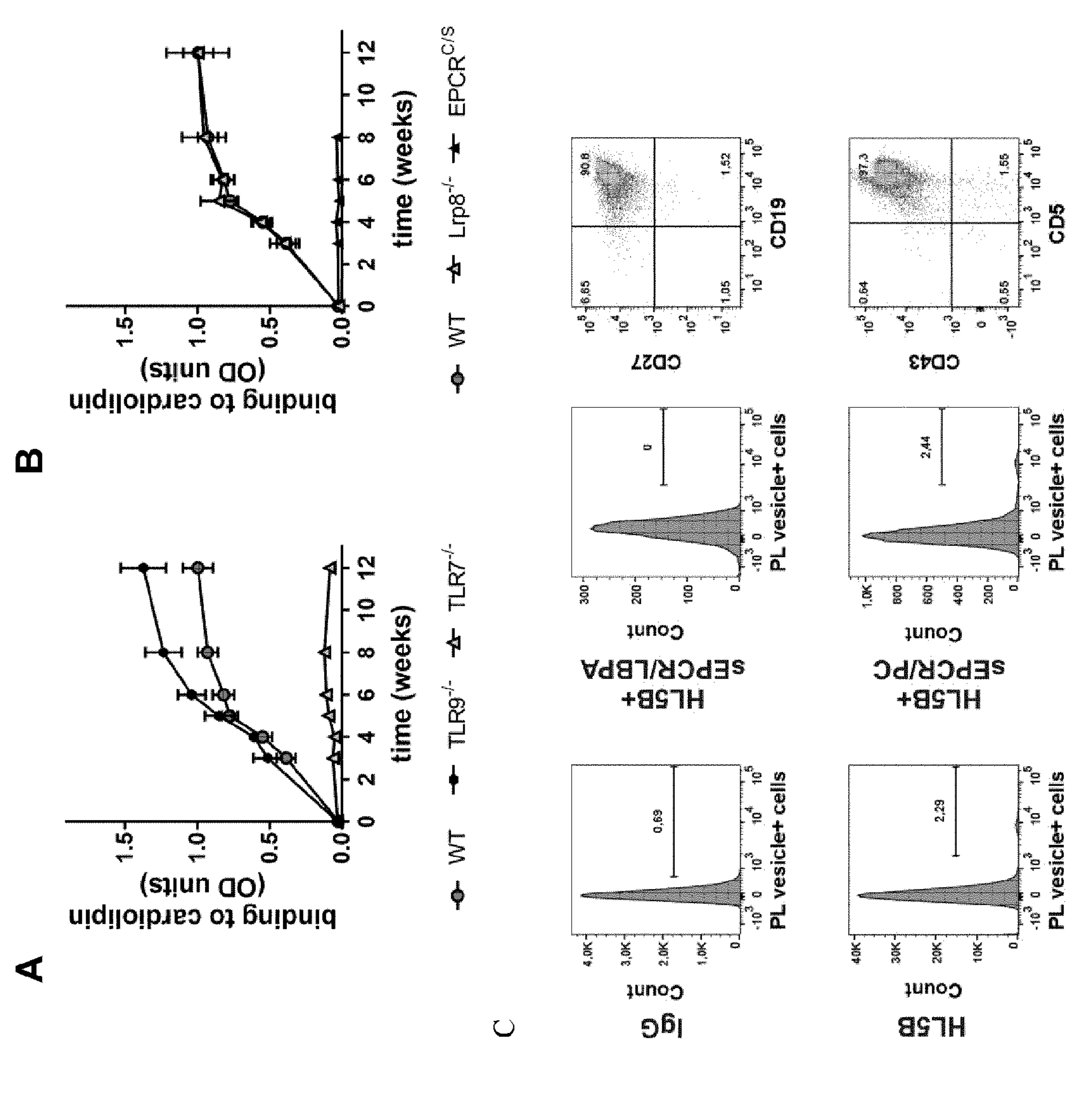
FIG. 10: shows that EPCR signalling drives aPL expansion in vivo. (A, B) Mice of the indicated genotypes were immunized with aPL HL5B or isotype matched control IgG and serum anti-cardiolipin titers were determined at the indicated times. (C) Cell reactive with negatively charged liposomes were only detected in mice immunized with aPL HL5B, but not isotype matched IgG. EPCR-LBPA, but not EPCR competed with liposome binding to these CD19+ CD5+CD43+CD27+ memory-type B1a cells(D) Immunization with human β2GPI induced a similar high titer IgG antibody response to human β2GPI in $EPCR^{WT}$ and $EPCR^{C/S}$ mice. (E) Antibody titers to LBPA, but not mouse prothrombin, were only detected in $EPCR^{WT}$, but not in $EPCR^{C/S}$ mice after 5 immunizations with human β2GPI. (F) IgG from human β2GPI-immunized $EPCR^{WT}$, but not $EPCR^{C/S}$ mice induced monocyte TF activity and proinflammatory signalling in monocytes.
Figure 10:
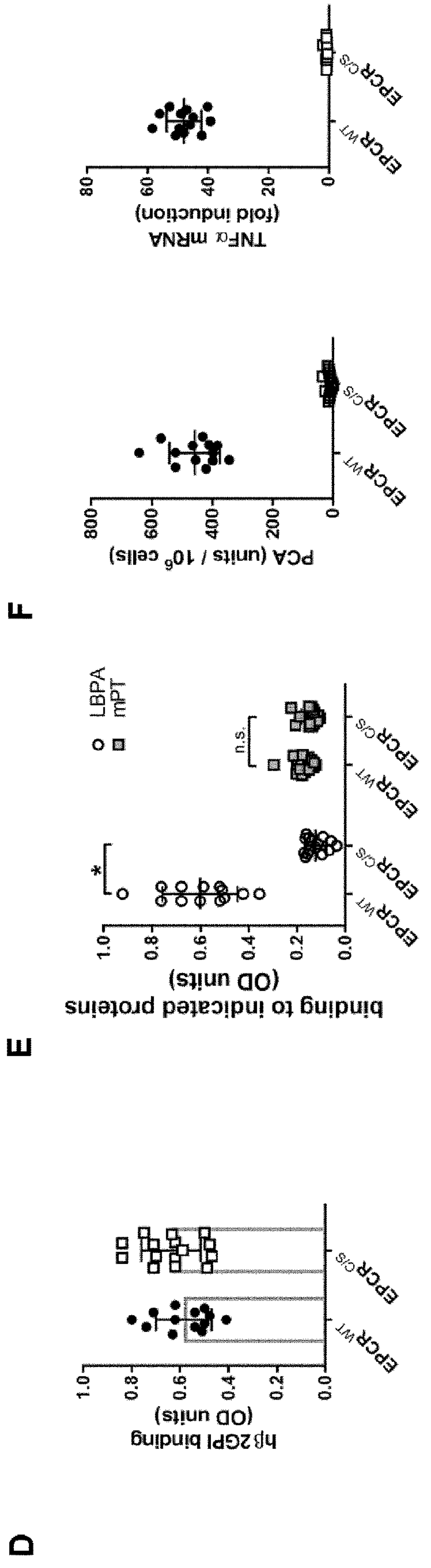

Therefore, the development of aPL in established models of APS was evaluated. Immunization with lipid-reactive monoclonal or polyclonal antibodies induces the appearance of cardiolipin-reactive antibodies in mice (42, 43). Immunization with aPL HL5B, but not control IgG, induced robust anti-cardiolipin titers within 3-6 weeks dependent on Tlr7, whereas $Tlr9^{-/-}$ mice displayed a slightly enhanced response (FIG. 10A). Immunization with aPL induced the appearance of circulating B1 cells reactive with labeled liposomes (44) and liposome staining was prevented by EPCR-LPBA, but not unmodified EPCR (FIG. 10B), indicating the expansion of EPCR-LPBA reactive B cells. Anti-cardiolipin titers did not develop in immunized $EPCR^{C/S}$ mice in sharp contrast to strain-matched WT controls as well as $LRP8^{-/-}$ mice (FIG. 10C). Thus, genetic ablation of EPCR signaling abolished the expansion of lipid-reactive antibodies triggered by immunization by pathogenic human aPL.

APS is also triggered by immunization with human β2GPI (45) which induced a similar high titer IgG antibody response to human β2GPI in $EPCR^{WT}$ and $EPCR^{C/S}$ mice (FIG. 10D). IgG titers to LBPA, but not prothrombin developed only in $EPCR^{WT}$ mice (FIG. 10E). In addition, only IgG from immunized $EPCR^{WT}$ mice induced TF activity and proinflammatory signaling in monocytes (FIG. 10F). Thus, EPCR is required for the development of autoimmunity in experimental APS.

Figure 11A:
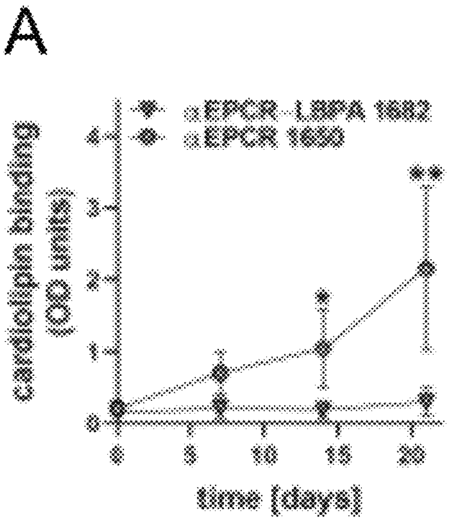
FIG. 11: shows the therapeutic relevance of an intervention in the EPCR-LBPA pathway in the exemplary context of autoimmunity and lupus erythematosus. (A) MRL-Faslpr lupus-prone mice were treated with the indicated αEPCR antibodies at an age of 4 weeks (day 0) and anti-cardiolipin titers were determined in serum at the indicated time points; n=5, *P=0.03; **P<0.0001; two-way ANOVA, Sidak's multiple comparisons test. (B) Antibodies to double stranded (ds) DNA were measured in αEPCR 1650- and αEPCR-LBPA 1682-treated MRL-Faslpr mice 2 weeks after the last dose or in 6-week-old MRL/MpJ control or MRL-Faslpr mice; n=4-5, *P<0.0001. (C) Immune cell infiltration of αEPCR-treated MRL-Faslpr mice; n=5, *P<0.025. (D) Renal pathology scores of αEPCR-treated MRL-Faslpr mice; n=5, *P=0.0317; Mann-Whitney U test.
Figure 11B:
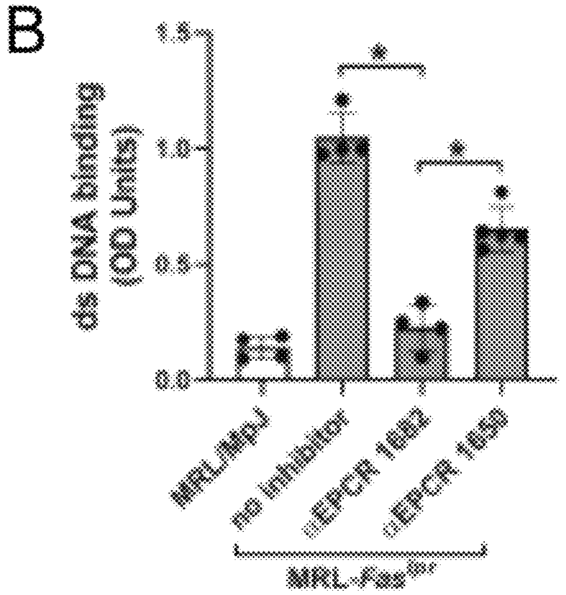
Figure 11C:
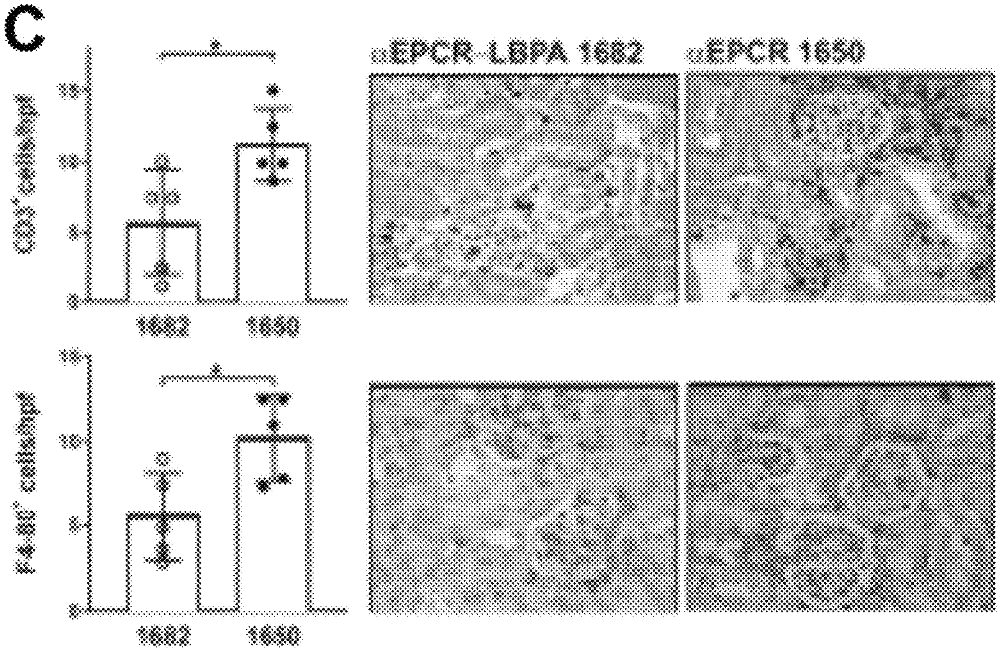
Figure 11D:
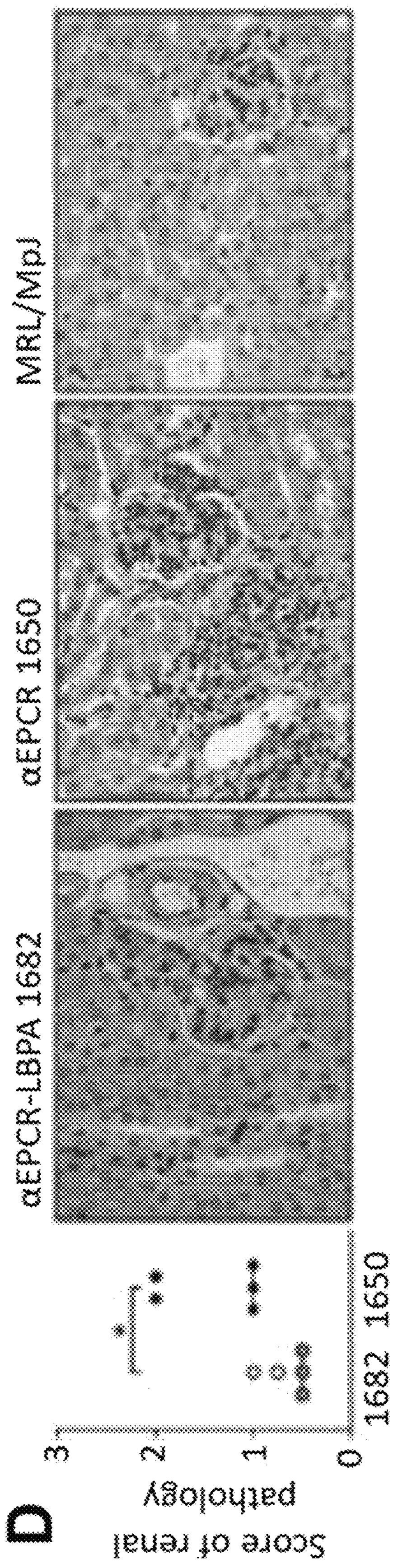

Example 6: EPCR-LBPA Signaling Drives aPL Expansion and Autoimmune Pathology In Vivo Specific inhibition of EPCR-LBPA completely prevented the development of aPLs (FIG. 11A) as well as double-stranded DNA autoantibodies, which were detectable already in 6-week-old MRL-Faslpr mice but not control MRL/MpJ mice (FIG. 11B). Treatment of MRL-Faslpr mice with αEPCR-LBPA 1682 not only reduced the development of autoantibodies but also protected from progressive kidney pathology as evidenced by reduced CD3+ and F4/80+ immune cell infiltration in the kidneys (FIG. 11C) and reduced renal pathology scores reflecting glomerular and interstitial damage (FIG. 11D).

Figure 12:
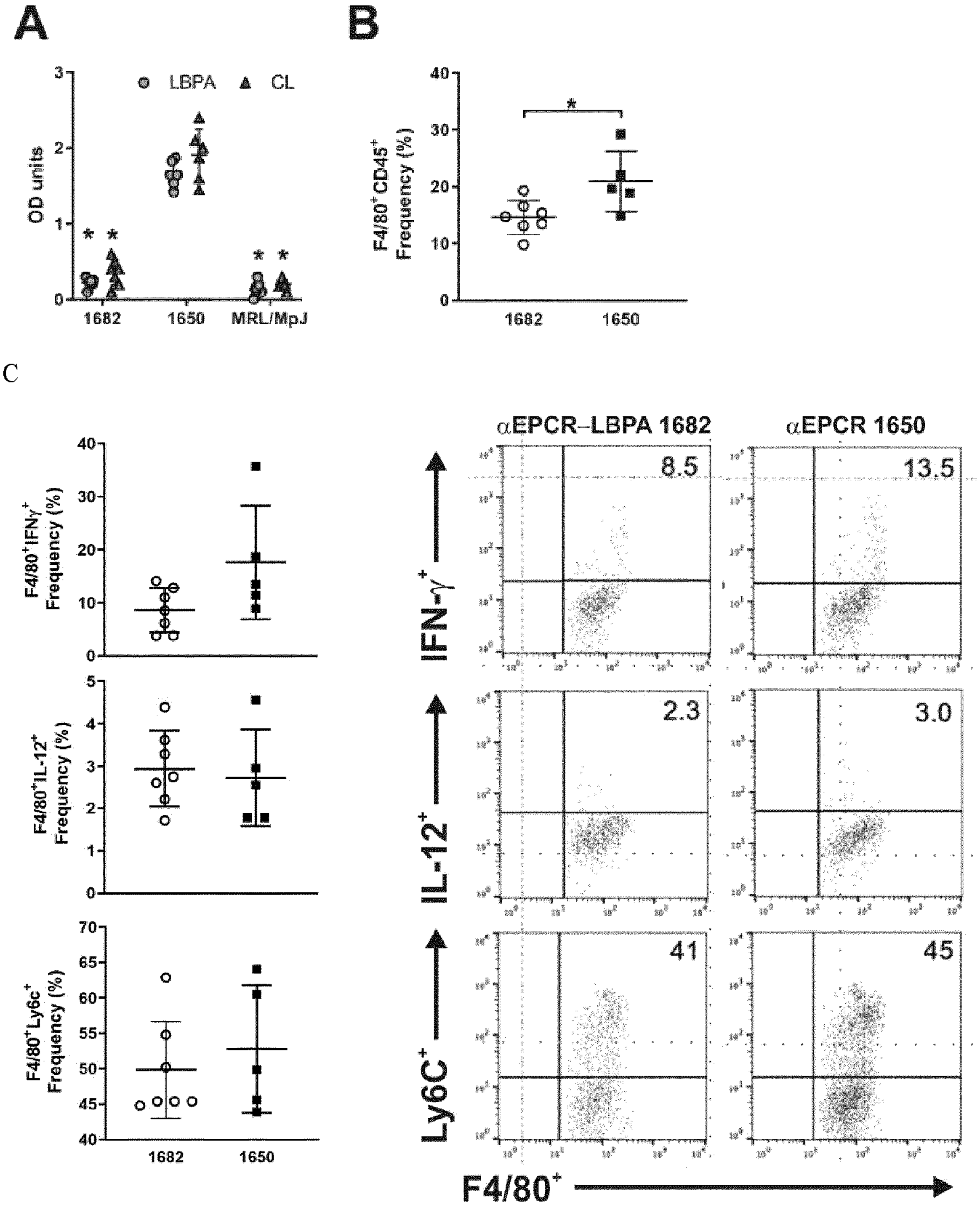
FIG. 12: shows that EPCR-LBPA is required for the development of autoimmune disease. (A) Reactivity of purified IgG (40 μg/ml) from MRL/MpJ control mice and from MRL-Faslpr mice treated with αEPCR 1650 or αEPCR-LBPA 1682 with immobilized LBPA or cardiolipin; n=6-7, * P<0.0001, different from control αEPCR 1650 treated mice; two-way ANOVA, Sidak's multiple comparisons test. (B) Infiltration of kidneys with CD45+/F4/80+ immune cells in MRL-Faslpr mice treated with non-inhibitory αEPCR 1650 or inhibitory αEPCR-LBPA 1682; n=5-7, *P=0.024. (C) Phenotype of F4/80+ cells in kidneys of MRL-Faslpr mice determined by cytokine staining. (D) Albuminuria in MRL/MpJ control mice and in MRL-Faslpr mice treated at the age of four weeks for six weeks with the indicated antibodies.
Figure 12:
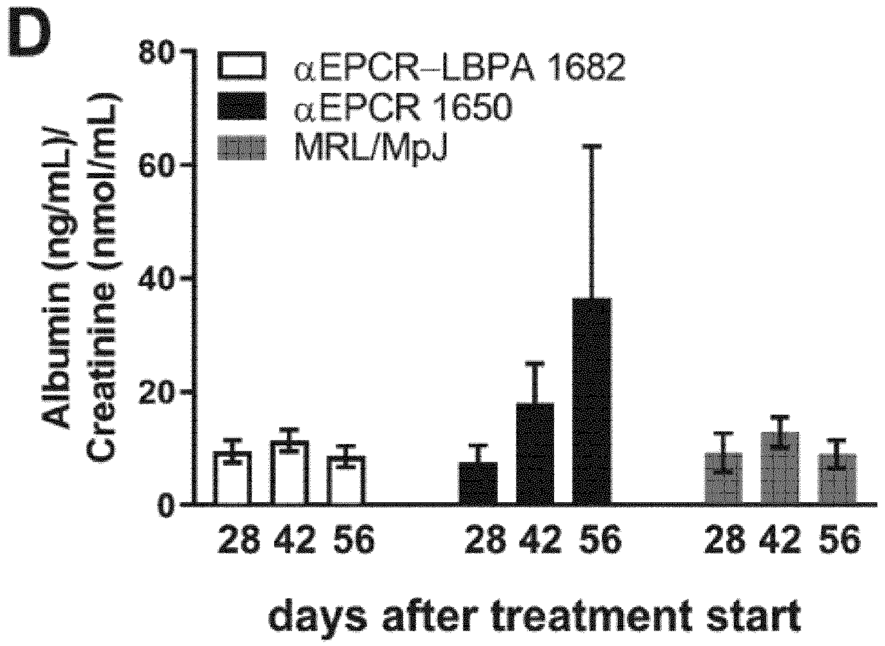

In an independent experiment, MRL-Faslpr mice were treated with αEPCR-LBPA 1682 or αEPCR 1650 for 6 weeks and analyzed 2 weeks after the end of treatment. αEPCR-LBPA 1682 again specifically suppressed serum αLBPA and αCL titers to levels seen in aged-matched MRL/MpJ control mice (FIG. 12A) and attenuated kidney infiltration of CD45+/F4/80+ immune cells measured by flow cytometry (FIG. 12B). These infiltrating myeloid cells expressed IFN-γ (FIG. 12C). Albuminuria only developed in mice treated with non-inhibitory αEPCR 1650, but not with inhibitory αEPCR-LBPA 1682 or in MRL/MpJ control mice (FIG. 12D). Thus, EPCR-LBPA signaling is crucial for both, the development of lipid-reactive antibodies as well as, more generally, drives kidney autoimmune pathology in this endosomal TLR7-dependent animal model.

REFERENCES

The references as cited herein are:

1. B. Giannakopoulos, S. A. Krilis, The pathogenesis of the antiphospholipid syndrome. N Engl J Med 368, 1033-1044 (2013).
2. K. Schreiber et al., Antiphospholipid syndrome. Nat Rev Dis Primers 4, 17103 (2018).
3. R. Bakimer et al., Induction of primary antiphospholipid syndrome in mice by immunization with a human monoclonal anticardiolipin antibody (H-3). J Clin Invest 89, 1558-1563 (1992).
4. S. S. Pierangeli, E. N. Harris, Induction of phospholipid-binding antibodies in mice and rabbits by immunization with human beta 2 glycoprotein 1 or anticardiolipin antibodies alone. Clin Exp Immunol 93, 269-272 (1993).
5. P. Lieby et al., The clonal analysis of anticardiolipin antibodies in a single patient with primary antiphospholipid syndrome reveals an extreme antibody heterogeneity. Blood 97, 3820-3828 (2001).
6. P. Redecha et al., Tissue factor: a link between C5a and neutrophil activation in antiphospholipid antibody induced fetal injury. Blood 110, 2423-2431 (2007).
7. D. Manukyan et al., Cofactor-independent human antiphospholipid antibodies induce venous thrombosis in mice. J. Thromb. Haemost 14, 1011-1020 (2016).
8. N. Muller-Calleja et al., Complement C5 but not C3 is expendable for tissue factor activation by cofactor-independent antiphospholipid antibodies. Blood Adv 2, 979-986
9. N. Prinz et al., Antiphospholipid antibodies induce translocation of TLR7 and TLR8 to the endosome in human monocytes and plasmacytoid dendritic cells. Blood 118, 2322-2332 (2011).
10. N. Prinz, N. Clemens, A. Canisius, K. J. Lackner, Endosomal NADPH-oxidase is critical for induction of the tissue factor gene in monocytes and endothelial cells. Lessons from the antiphospholipid syndrome. Thromb. Haemost 109, 525-531 (2013).
11. N. Muller-Calleja et al., Antiphospholipid antibody-induced cellular responses depend on epitope specificity: implications for treatment of antiphospholipid syndrome. J. Thromb. Haemost 15, 2367-2376 (2017).
12. Z. Romay-Penabad et al., Apolipoprotein E receptor 2 is involved in the thrombotic complications in a murine model of the antiphospholipid syndrome. Blood 117, 1408-1414 (2011).
13. V. Ulrich et al., ApoE Receptor 2 Mediation of Trophoblast Dysfunction and Pregnancy Complications Induced by Antiphospholipid Antibodies in Mice. Arthritis Rheumatol 68, 730-739 (2016).
14. N. Müller-Calleja et al., Tissue factor pathway inhibitor primes monocytes for antiphospholipid antibody-induced thrombosis. Blood, (2019).
15. J. Disse et al., The Endothelial Protein C Receptor Supports Tissue Factor Ternary Coagulation Initiation Complex Signaling through Protease-activated Receptors. J Biol. Chem 286, 5756-5767 (2011).
16. H. P. Liang et al., EPCR-dependent PAR2 activation by the blood coagulation initiation complex regulates LPS-triggered interferon responses in mice. Blood 125, 2845-2854 (2015).
17. R. K. Sinha et al., Apolipoprotein E Receptor 2 Mediates Activated Protein C-Induced Endothelial Akt Activation and Endothelial Barrier Stabilization. Arterioscler. Thromb.
Vasc. Biol 36, 518-524 (2016).
18. F. J. Castellino et al., Mice with a severe deficiency of the endothelial protein C receptor gene develop, survive, and reproduce normally, and do not present with enhanced arterial thrombosis after challenge. Thromb. Haemost 88, 462-472 (2002).
19. S. S. Pierangeli et al., Requirement of activation of complement C3 and C5 for antiphospholipid antibody-mediated thrombophilia. Arthritis Rheum 52, 2120-2124 (2005).
20. F. Fischetti et al., Thrombus formation induced by antibodies to beta2-glycoprotein I is complement dependent and requires a priming factor. Blood 106, 2340-2346 (2005).
21. G. Girardi et al., Complement C5a receptors and neutrophils mediate fetal injury in the antiphospholipid syndrome. J. Clin. Invest 112, 1644-1654 (2003).
22. F. Langer et al., Rapid activation of monocyte tissue factor by antithymocyte globulin is dependent on complement and protein disulfide isomerase. Blood 121, 2324-2335 (2013).
23. A. S. Rothmeier et al., Identification of the integrin-binding site on coagulation factor VIIa required for proangiogenic PAR2 signaling. Blood 131, 674-685 (2018).
24. V. Hurtado et al., Autoantibodies against EPCR are found in antiphospholipid syndrome and are a risk factor for fetal death. Blood 104, 1369-1374 (2004).
25. I. Ott et al., Reversible regulation of tissue factor-induced coagulation by glycosyl phosphatidylinositol-anchored tissue factor pathway inhibitor. Arterioscler. Thromb.
Vasc. Biol 20, 874-882 (2000).
26. V. Oganesyan et al., The crystal structure of the endothelial protein C receptor and a bound phospholipid. J. Biol. Chem 277, 24851-24854 (2002).
27. J. Lopez-Sagaseta et al., sPLA2-V inhibits EPCR anticoagulant and antiapoptotic properties by accommodating lysophosphatidylcholine or PAF in the hydrophobic groove. Blood 119, 2914-2921 (2012).
28. T. Kobayashi et al., A lipid associated with the antiphospholipid syndrome regulates endosome structure and function. Nature 392, 193-197 (1998).
29. J. Wang, U. R. Pendurthi, L. V. M. Rao, Sphingomyelin encrypts tissue factor: ATP-induced activation of A-SMase leads to tissue factor decryption and microvesicle shedding. Blood Adv 1, 849-862 (2017).
30. W. M. Kuebler et al., Thrombin stimulates albumin transcytosis in lung microvascular endothelial cells via activation of acid sphingomyelinase. Am. J. Physiol Lung Cell Mol. Physiol 310, L720-L732 (2016).

31. P. Munzer et al., Acid sphingomyelinase regulates platelet cell membrane scrambling, secretion, and thrombus formation. Arterioscler. Thromb. Vasc. Biol 34, 61-71 (2014).

32. H. Grassme et al., CD95 signaling via ceramide-rich membrane rafts. J. Biol. Chem 276, 20589-20596 (2001).

33. V. O. Oninla, B. Breiden, J. O. Babalola, K. Sandhoff, Acid sphingomyelinase activity is regulated by membrane lipids and facilitates cholesterol transfer by NPC2. J. Lipid Res 55, 2606-2619 (2014).

34. S. Subramaniam et al., Distinct contributions of complement factors to platelet activation and fibrin formation in venous thrombus development. Blood 129, 2291-2302 (2017).

35. C. Moratz et al., Regulation of systemic tissue injury by coagulation inhibitors in B6.MRL/lpr autoimmune mice. Clin Immunol 197, 169-178 (2018).

36. B. Isermann et al., The thrombomodulin-protein C system is essential for the maintenance of pregnancy. Nat. Med 9, 331-337 (2003).

37. H. P. Liang et al., Coagulation factor V mediates inhibition of tissue factor signaling by activated protein C in mice. Blood 126, 2415-2423 (2015).

38. C. Perez-Sanchez et al., Gene profiling reveals specific molecular pathways in the pathogenesis of atherosclerosis and cardiovascular disease in antiphospholipid syndrome, systemic lupus erythematosus and antiphospholipid syndrome with lupus. Ann. Rheum. Dis 74, 1441-1449 (2015).

39. E. Palli, E. Kravvariti, M. G. Tektonidou, Type I Interferon Signature in Primary Antiphospholipid Syndrome: Clinical and Laboratory Associations. Front Immunol 10, 487 (2019).

40. A. Sang et al., Innate and adaptive signals enhance differentiation and expansion of dual-antibody autoreactive B cells in lupus. Nat Commun 9, 3973 (2018).

41. B. Giannakopoulos et al., Deletion of the antiphospholipid syndrome autoantigen beta2-glycoprotein I potentiates the lupus autoimmune phenotype in a Toll-like receptor 7-mediated murine model. Arthritis Rheumatol 66, 2270-2280 (2014).

42. S. S. Pierangeli, E. N. Harris, Induction of phospholipid-binding antibodies in mice and rabbits by immunization with human beta 2 glycoprotein 1 or anticardiolipin antibodies alone. Clin Exp Immunol 93, 269-272 (1993).

43. R. Bakimer et al., Induction of primary antiphospholipid syndrome in mice by immunization with a human monoclonal anticardiolipin antibody (H-3). J Clin Invest 89, 44. P. Lieby et al., The clonal analysis of anticardiolipin antibodies in a single patient with primary antiphospholipid syndrome reveals an extreme antibody heterogeneity. Blood 97, 3820-3828 (2001).

45. A. E. Gharavi, L. R. Sammaritano, J. Wen, K. B. Elkon, Induction of antiphospholipid autoantibodies by immunization with beta 2 glycoprotein I (apolipoprotein H). J Clin Invest 90, 1105-1109 (1992).

The invention claimed is:

1. A method for identifying an inhibitor of endothelial protein C receptor (EPCR) function in an autoimmune disease, wherein said autoimmune disease is selected from the group consisting of antiphospholipid syndrome (APS), primary Sjögren syndrome, rheumatoid arthritis, systemic lupus erythematosus, and lupus nephritis, the method comprising:

i) providing a biological sample comprising an EPCR protein, ii) contacting a potential inhibitor with said sample, iii) adding LBPA to the sample, iv) testing binding of LBPA to said EPCR protein in the presence of said potential inhibitor, and iv) identifying said potential inhibitor based on said LBPA-binding as tested.

2. The method according to claim 1, wherein at least one of EPCR, LBPA, and/or said potential inhibitor is suitably labelled and/or immobilized.

3. The method according to claim 1, further comprising the step of testing said potential inhibitor as identified for being an inhibitor of endothelial protein C receptor (EPCR) function in autoimmune disease while not inhibiting regulatory functions of EPCR in coagulation.

4. The method according to claim 1, wherein said potential inhibitor is selected from the group consisting of a small molecule, a protein, a peptide, an antibody or antigen-binding fragment thereof, an enzyme, and an aptamer.

5. The method according to claim 1, wherein the autoimmune disease is antiphospholipid syndrome (APS).

6. The method according to claim 1, wherein the autoimmune disease is primary Sjögren syndrome.

7. The method according to claim 1, wherein the autoimmune disease is rheumatoid arthritis.

8. The method according to claim 1, wherein the autoimmune disease is systemic lupus erythematosus.

9. The method according to claim 1, wherein the autoimmune disease is lupus nephritis.

* * * * *